(12) United States Patent
Liang et al.

(10) Patent No.: US 7,458,685 B2
(45) Date of Patent: Dec. 2, 2008

(54) AUTOMATED FUNDUS IMAGING SYSTEM

(75) Inventors: Rongguang Liang, Penfield, NY (US);
Dale L. Tucker, Rochester, NY (US);
Jeffery R. Hawver, Marion, NY (US);
Seung-Ho Baek, Pittsford, NY (US);
Vishwas G. Abhyankar, Pittsford, NY (US); Richard Weil, Pittsford, NY (US);
Douglass L. Blanding, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 190 days.

(21) Appl. No.: 11/196,824

(22) Filed: Aug. 3, 2005

(65) Prior Publication Data

US 2007/0030450 A1 Feb. 8, 2007

(51) Int. Cl.
A61B 3/14 (2006.01)

(52) U.S. Cl. .......................... 351/206; 351/211; 396/18

(58) Field of Classification Search ................. 351/206, 351/211; 396/18
See application file for complete search history.

(56) References Cited

U.S. PATENT DOCUMENTS

| 4,732,466 | A | 3/1988 | Humphrey |
| 4,838,680 | A | 6/1989 | Nunokawa |
| 5,572,266 | A | 11/1996 | Ohtsuka |
| 5,713,047 | A | 1/1998 | Kohayakawa |
| 5,943,116 | A | 8/1999 | Zeimer |
| 6,296,358 | B1 | 10/2001 | Cornsweet et al. |
| 6,546,198 | B2 | 4/2003 | Ohtsuka |
| 6,636,696 | B2 | 10/2003 | Saito |
| 6,705,726 | B2 | 3/2004 | Tanassi et al. |
| 6,733,129 | B2 | 5/2004 | Masaki |
| 6,830,336 | B2 | 12/2004 | Fransen |
| 7,219,996 | B2 * | 5/2007 | Ichikawa ..................... 351/206 |
| 2004/0114107 | A1 * | 6/2004 | Mimura ....................... 351/208 |

* cited by examiner

*Primary Examiner*—Joseph Martinez

(57) ABSTRACT

An apparatus for obtaining a retinal image of an eye has a control logic processor (214) for executing a sequence of operations for obtaining the image. A visual target (162) orients the eye of a patient when viewed. An indicator element (410) provides a signal that indicates that the patient is in position. A cornea focus detection section (450) indicates cornea focus, in cooperation with the control logic processor (214). An alignment actuator aligns the optical path according to a signal obtained from the cornea focus detection section (450). A retina focus detection section (452) detects retina focus in cooperation with the control logic processor (214). A focusing actuator (406) is controlled by instructions from the control logic processor (214) according to a signal obtained from the retina focus detection section (452). An image capture light source is energized by the control logic processor (214) for illuminating the retina.

23 Claims, 30 Drawing Sheets

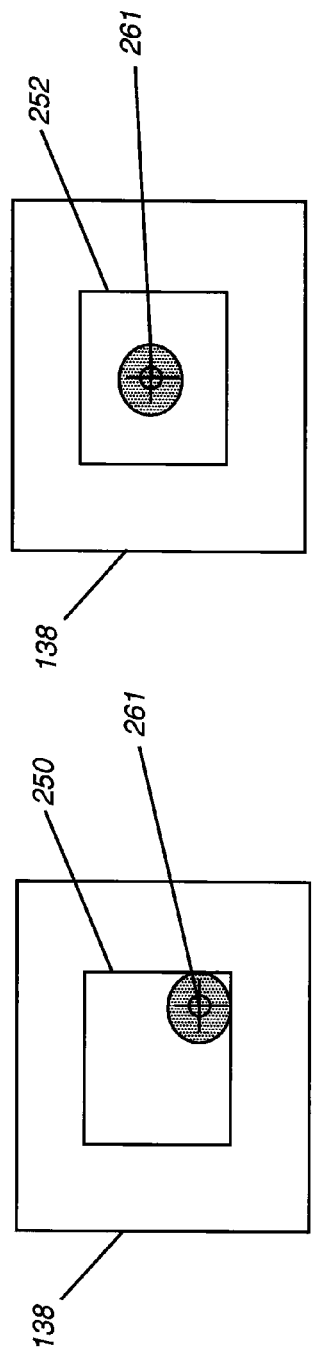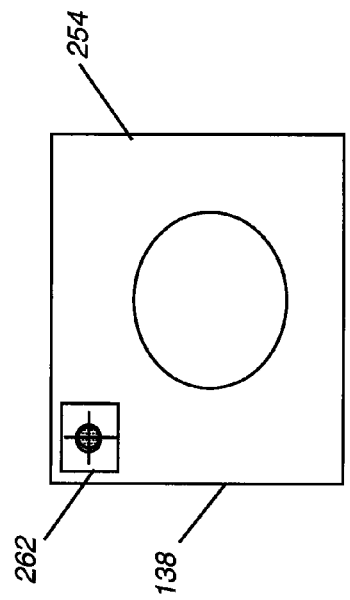
FIG. 8A PRIOR ART
FIG. 8B PRIOR ART
FIG. 8C PRIOR ART

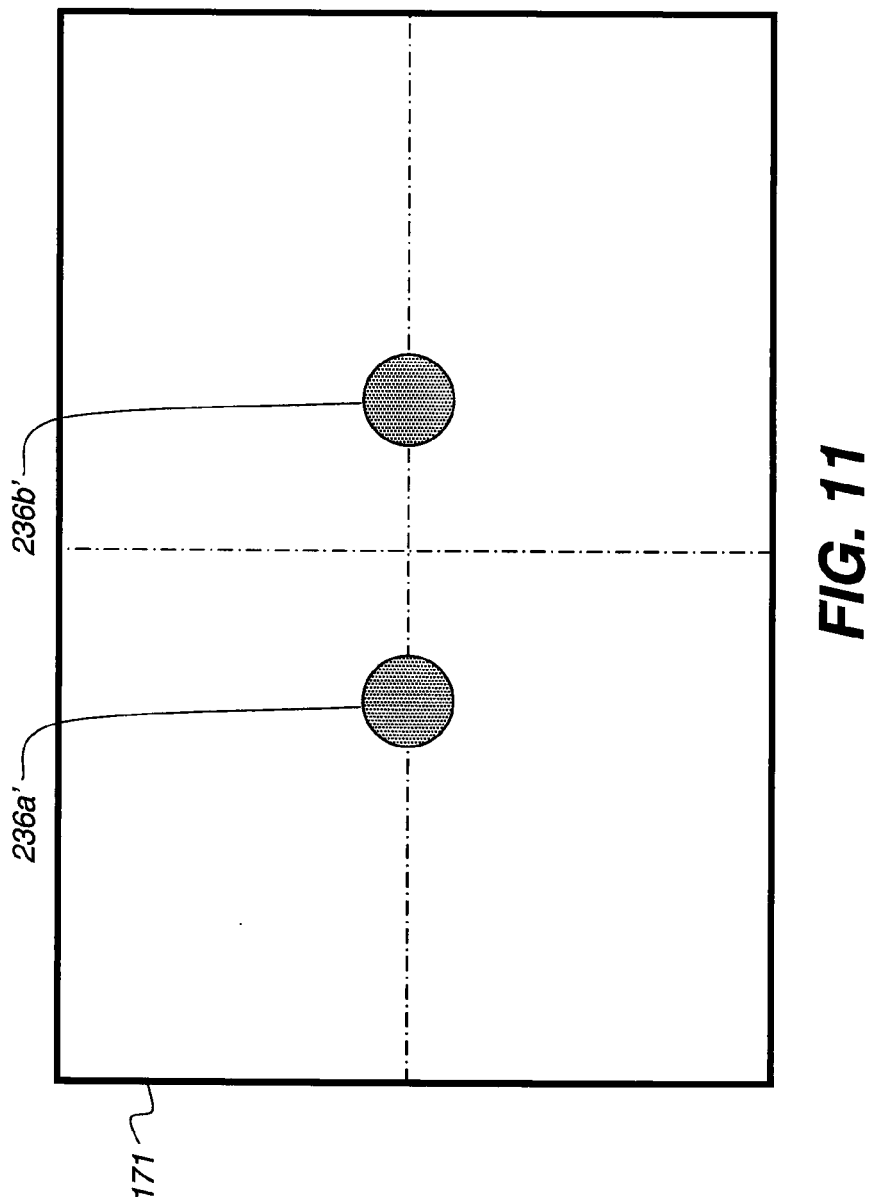

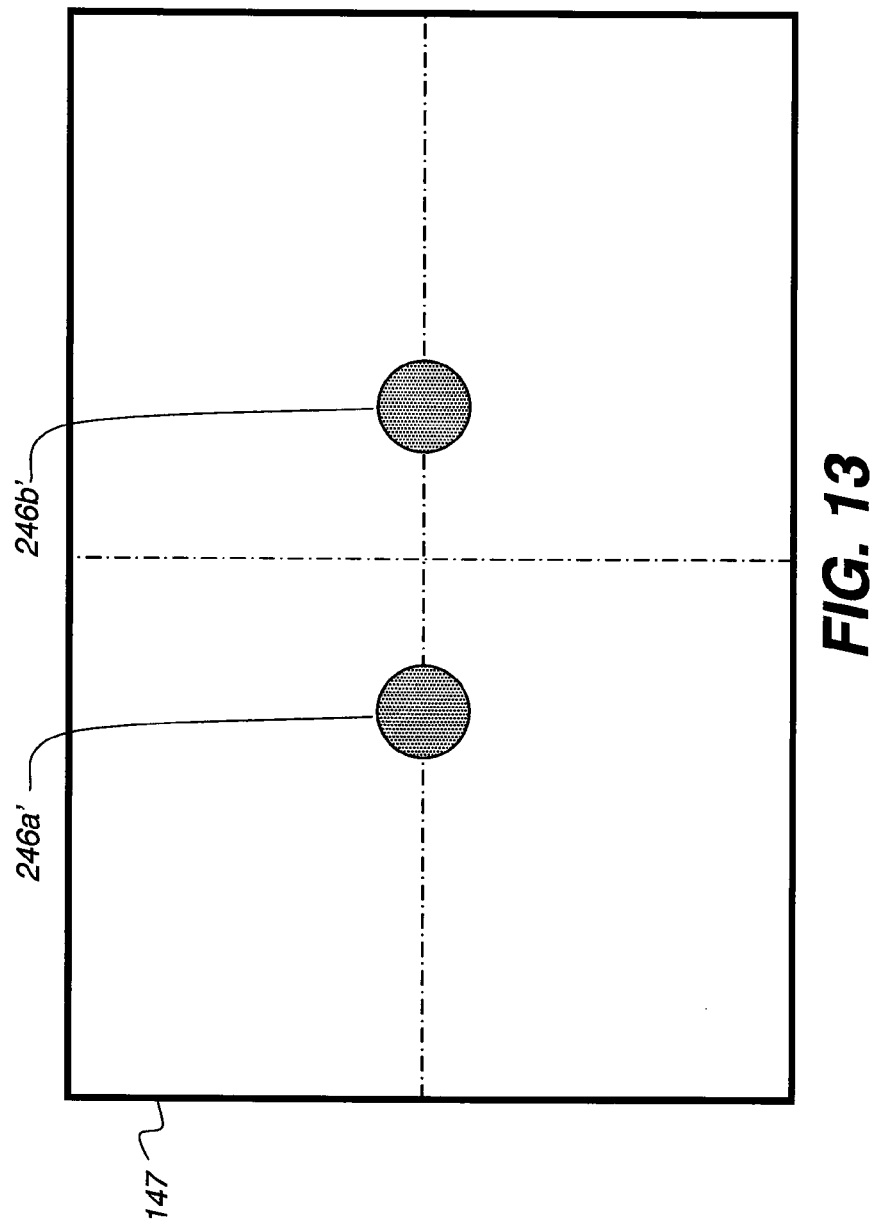

AUTOMATED FUNDUS IMAGING SYSTEM

FIELD OF THE INVENTION

This invention generally relates to electronic imaging apparatus for fundus imaging and more particularly relates to an improved fundus imaging apparatus for automated imaging without operator intervention.

BACKGROUND OF THE INVENTION

Fundus camera imaging is acknowledged to be an important diagnostic tool for detection of various conditions affecting the eye, including diabetic retinopathy and macular degeneration. Various embodiments of fundus imaging apparatus are disclosed, for example in U.S. Pat. Nos. 5,713,047 (Kohayakawa); 5,943,116 (Zeimer); 5,572,266 (Ohtsuka); 4,838,680 (Nunokawa); 6,546,198 (Ohtsuka); and 6,636,696 (Saito).

While conventional fundus imaging apparatus require manual operation, there has been considerable effort expended toward automating specific functions of these imaging apparatus. For example, U.S. Pat. No. 6,296,358 (Cornsweet et al.) discloses an automated sequence that is executed for pupil alignment and focusing. U.S. Pat. No. 4,732,466 (Humphrey) discloses an automated focus mechanism for a fundus imaging apparatus. U.S. Pat. No. 6,733,129 (Masaki) discloses an automatic alignment sequence using a feedback loop with a light beam projected onto the cornea, a sensor for sensing reflected light, and a series of motors for effecting alignment adjustment. U.S. Pat. No. 6,705,726 (Tanassi et al.) discloses a multi-function optical imaging apparatus with a number of automation features in various subsystems. U.S. Pat. No. 6,830,336 (Fransen) discloses automation of the sequencing of images for a patient, in order to obtain a complete series of fundus images once the patient is properly positioned and suitable focus has been achieved.

While these patents attest to continuous improvements in fundus camera design, there are still significant hurdles to widespread acceptance and usability of these devices. Among disadvantages noted with current apparatus are relative complexity of operation. This remains the case even with improvements that automate focus and alignment operations, as noted above.

A number of fundus imaging apparatus are designed for the more limited function of diabetic retinopathy screening. These devices are intended to be used by relatively unskilled operators who receive minimal training. For example, these lower cost fundus imaging apparatus are intended to be installed at a personal care physician (PCP) office or in medical test lab collection facility, rather than at a specialist's facility. The intent is to have these apparatus operated by a clerical staff of medical technicians at the PCP office of other site, to obtain images for first-level screening. In order to provide simple operation, these fundus imaging apparatus are designed with an operator interface that provides controls for operation, with operator feedback as well as automated response to events such as patient head and eye movement.

While recent designs appear to offer better usability and performance of these systems, however, there remains considerable room for improvement. One inherent problem relates to the operator learning curve. While a number of these systems offer ease of operation, they still require some amount of practice. An operator working with a fundus imaging apparatus can achieve some facility after working continuously with such a system for an hour or so, particularly under trained guidance. However, only a small percentage of patients in the PCP environment will require this type of screening. Operating this equipment once or twice a day may not give an operator enough practice to achieve a level of mastery of the apparatus. Moreover, problems of staff scheduling and turnover may make it impractical for a facility to have only a single staff member trained to use this apparatus. Thus, even though newer fundus imaging apparatus may be easier to operate, there are inherent barriers to taking advantage of easier operation. In order to be economical, classroom or individual training is impractical. Instead, operator training must be delivered in electronic form, such as by CD or over the Internet, or by means of a manual or quick-reference guide. Even using on-screen prompts, it would be very difficult to provide effective interactive operator assistance during imaging.

There is a need for an improved fundus imaging apparatus that is essentially operable without operator intervention. This would make it possible, for example, to have an imaging system that is automated or is even operable by patients themselves, with minimal setup instruction from PCP staff members.

SUMMARY OF THE INVENTION

Briefly, according to one aspect of the present invention, an apparatus for obtaining a retinal image from an eye, comprises:
  a) a control logic processor for executing a sequence of operations for obtaining the image;
  b) a visual target for orienting the eye of a patient when the target is viewed by the patient;
  c) an indicator element for providing a signal that indicates that the patient is in position for imaging;
  d) a cornea focus detection section for providing an indication of cornea focus, in cooperation with the control logic processor;
  e) an alignment actuator for aligning the optical path of the apparatus according to a signal obtained from the cornea focus detection section;
  f) a retina focus detection section for detecting retina focus in cooperation with the control logic processor;
  g) a focusing actuator controlled by instructions from the control logic processor according to a signal obtained from the retina focus detection section; and
  h) an image capture light source energized by the control logic processor for illuminating the retina for image capture.

It is a feature of the present invention that it provides an automated apparatus that does not require operator intervention for normal operation.

It is an advantage of the present invention that it can allow the patient to have an enhanced sense of control over the imaging process, without requiring operational expertise or training of the patient.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

FIGS. 8A, 8B, and 8C are plan views showing an arrangement of operator interface display screens for a conventional fundus imaging apparatus;

FIG. 11 is a plan view of the sensor field for cornea focus;

FIG. 13 is a plan view of the sensor field for retina focus;

DETAILED DESCRIPTION OF THE INVENTION

The present description is directed in particular to elements forming part of, or cooperating more directly with, apparatus in accordance with the invention. It is to be understood that elements not specifically shown or described may take various forms well known to those skilled in the art.

Figure 1:
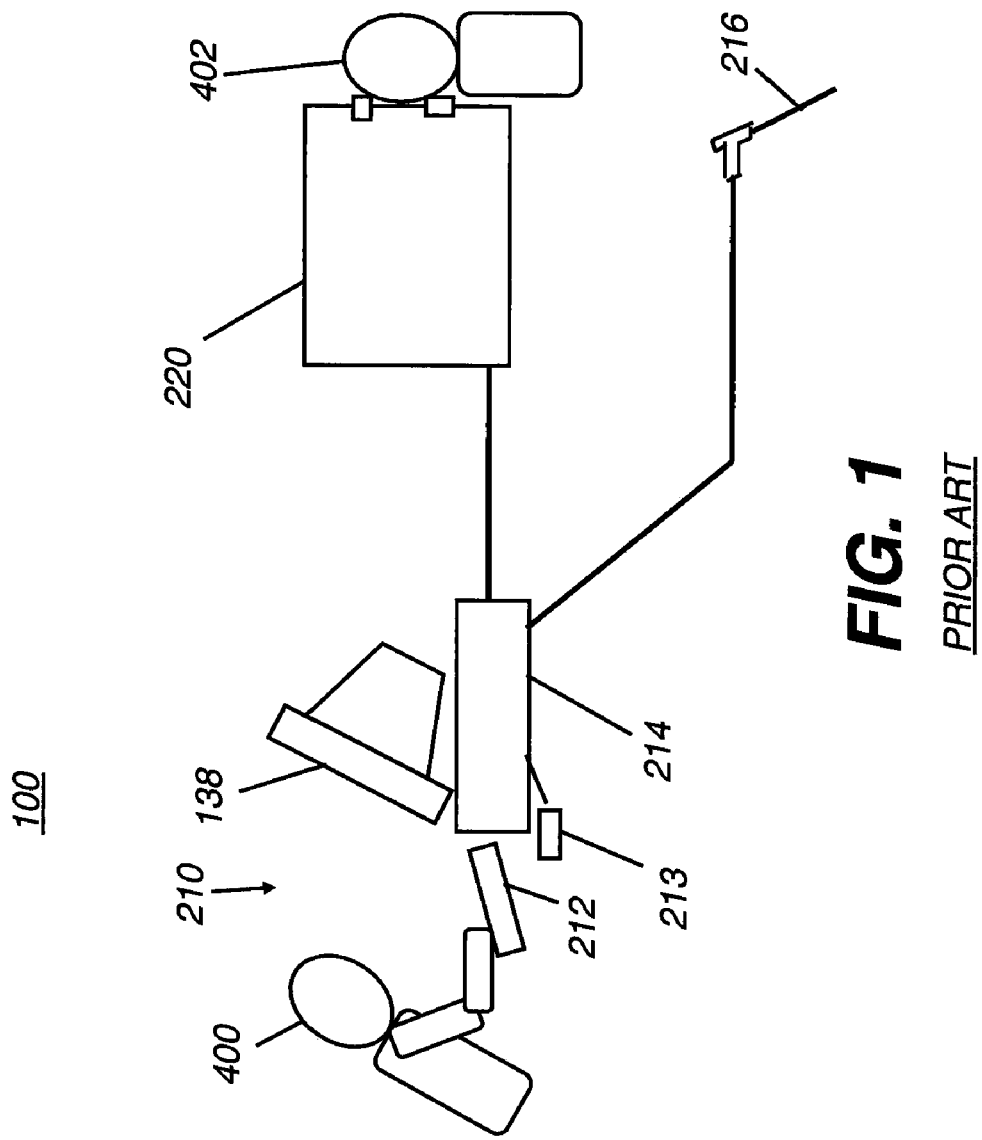
FIG. 1 is a schematic block diagram of a fundus imaging apparatus.

System Configuration Referring to FIG. 1, there is shown a conventional fundus imaging system 100 for obtaining an image from a patient 402. To support fundus imaging system 100, a control workstation 210 has a display 138, a keyboard 212, and a control logic processor 214 for providing control logic and interface functions for an operator 400. Imaging functions are provided by optical, electro-optical, and electronic components within a fundus imaging appliance 220. A network 216 allows communication between fundus imaging system 100 and processing and storage devices at other networked sites. Using network 216, for example, fundus images obtained by fundus imaging system 100 can be uploaded to other sites, such as to sites where diagnostic assessment is performed remotely. Alternately, software, instructions, or other data could be downloaded from other networked sites to fundus imaging system 100 or to control workstation 210.

There are a number of alternate embodiments possible based on the overall arrangement of FIG. 1. For example, the function of control logic processor 214 may be performed by logic components within fundus imaging appliance 220, rather than by a separately packaged processor, as shown in FIG. 1. Thus, camera interface devices, operating controls, and display could be located on the body of fundus imaging appliance 220 itself, for example. Operator interface functions provided by display 138 and keyboard 212 could be combined in a touchscreen console, for example. The connection to network 216 may be a standard Ethernet connection, a dedicated network telecommunications connection, or a dial-up modem. In one embodiment, network 216 allows wireless connection. Alternately, the connection to network 216 may be dispensed with altogether, such that imaging appliance 220 records fundus imaging data onto a data storage medium such as a removable storage medium, which could be as a magnetic, electronic, or optical storage medium, for example.

Fundus Imaging Appliance 220 Block Diagram

Figure 2:
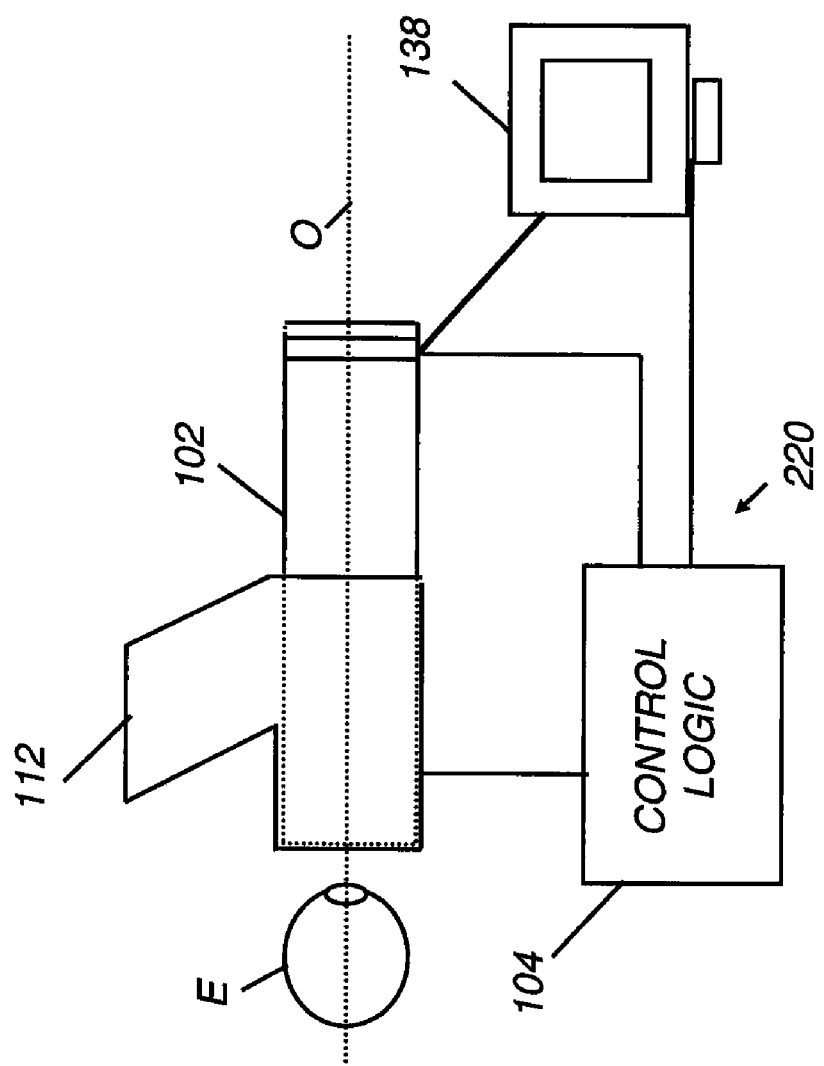
FIG. 2 is a schematic block diagram showing subsystem components of the imaging apparatus of the present invention.

Referring to FIG. 2, there is shown a high-level schematic block diagram of key subsystems of fundus imaging appliance 220. The relative position of eye E is shown on an optical axis O. Alignment of illumination and imaging optics and delivery of light to the eye is performed by an illumination section 112. An image capture section 102 then cooperates with illumination section 112 components to obtain the retinal images from eye E. A control logic processor 104 within fundus imaging appliance 220 controls illumination section 112 and image capture section 102 components to maintain proper alignment relative to eye E and provide the optimal lighting characteristics for retinal imaging. Control logic processor 104 also executes pupil-tracking algorithms and provides signals for controlling imaging operation. Operator commands at control workstation 210 (FIG. 1) are provided to control logic processor 104 for manipulating component positioning, illumination, and imaging functions.

Illumination Arrangement

Figure 3:
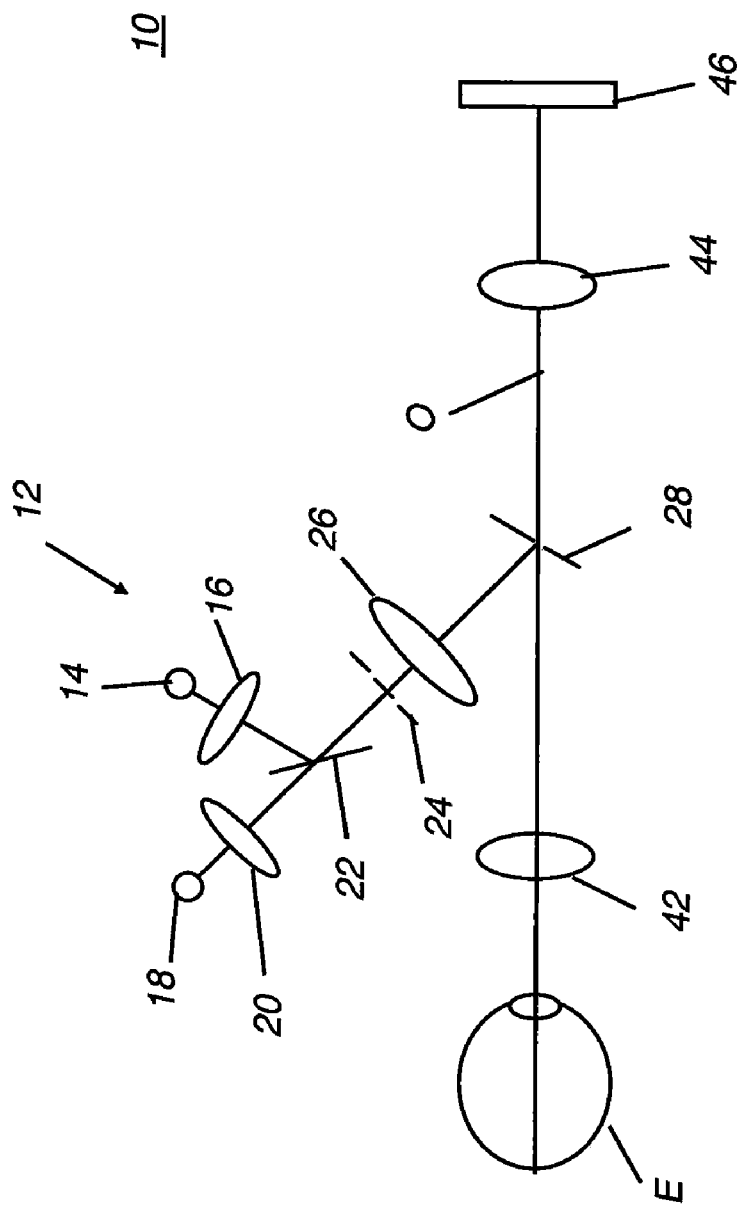
FIG. 3 is a schematic block diagram showing the overall arrangement of illumination apparatus components within a conventional fundus imaging apparatus.

Referring to FIG. 3, there is shown a schematic diagram of a fundus imaging apparatus 10 in which a conventional illumination section 12 is used. The patient's eye E is positioned along an optical axis O using an alignment subsystem, not shown in FIG. 3, but described subsequently. Illumination section 12 directs light either from an observation light source 14 and a lens 16 or from an image capture light source 18 and a lens 20 as controlled by control logic circuitry (not shown in FIG. 3). A half-mirror 22 directs light from the appropriate source through a ring-slit diaphragm 24 and a lens 26, to an apertured mirror 28. Apertured mirror 28 directs the illumination light along axis O and toward the pupil for illuminating the retina of eye E. Depending on the use of fundus imaging apparatus 10 at any one time, either observation light source 14 or image capture light source 18 are activated. Observation light source 14 is typically infrared (IR) light, to which eye E is insensitive. Image capture light source 18, on the other hand, may be a high-brightness source such as a xenon lamp, for example. Depending on the application, image capture light source 18 may be pulsed or strobed.

Figure 4:
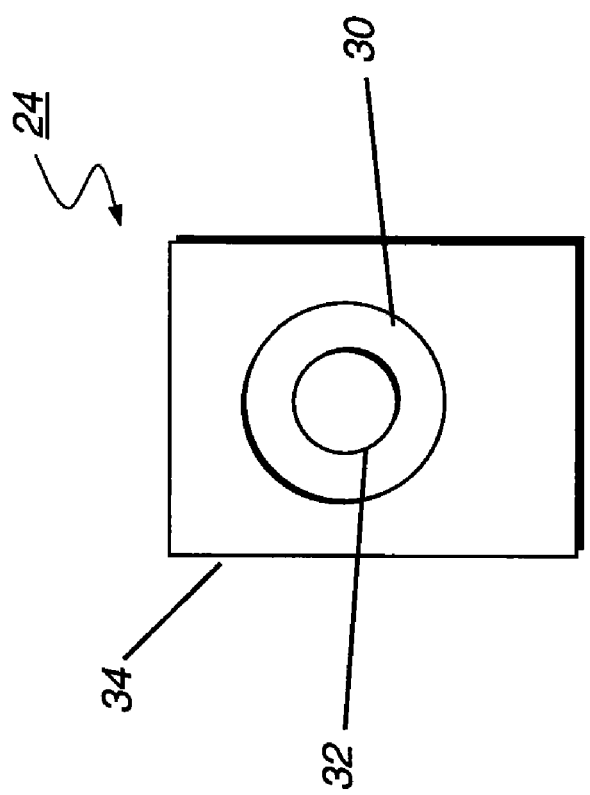
FIG. 4 is a plan view of a ring-slit diaphragm used in a conventional fundus imaging apparatus.
Figure 5:
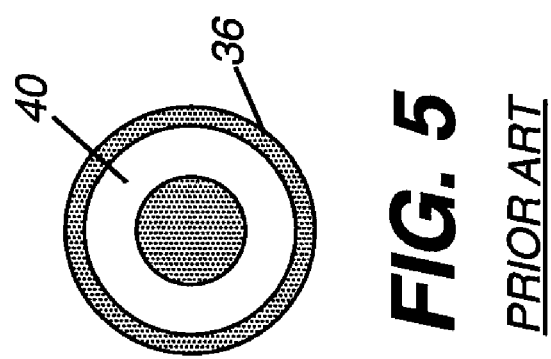
FIG. 5 is a plan view representation of the ring of illumination applied to the pupil of a patient in a conventional apparatus.

Ring-slit diaphragm 24 has the characteristic functional arrangement shown in FIG. 4. Light is transmitted through an inner ring 30 and is blocked at a middle section 32 and at an outer section 34. As is shown in the received illumination ring of FIG. 5, inner ring 30 is directed into a pupil 36 of the patient as a ring 40 of illumination. To obtain the retinal image, apertured mirror 28 (FIG. 3) has an aperture suitably centered about optical axis O to allow light that has been reflected from the retina of eye E and directed through lenses 42 and 44 to a sensor 46, such as a charge coupled device (CCD).

Figure 6:
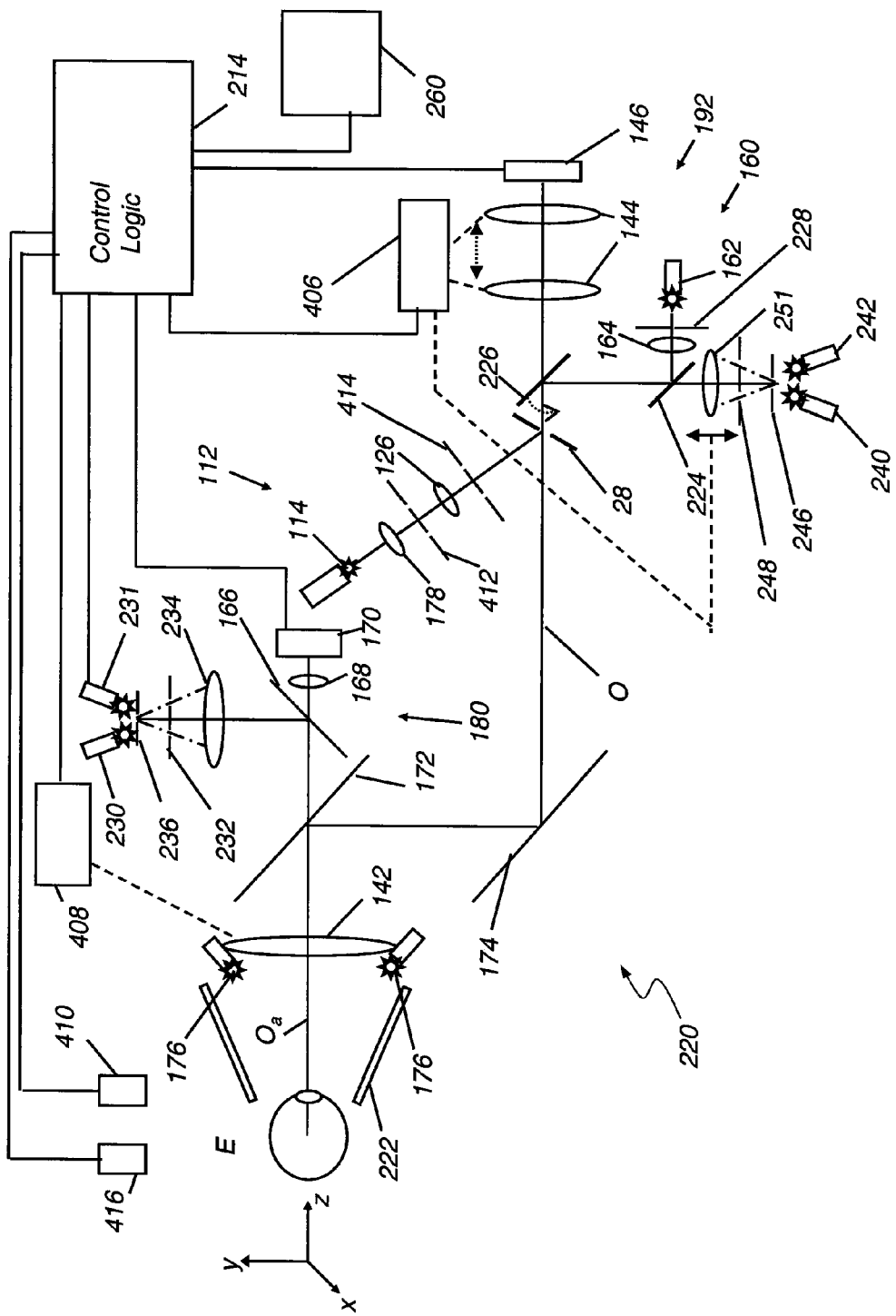
FIG. 6 is a schematic block diagram of a fundus imaging apparatus in one embodiment.

Referring to FIG. 6, there is shown a more detailed block diagram of fundus imaging appliance 220 optical components in one embodiment of the present invention. In addition to illumination section 112 described above, fundus imaging appliance 220 has an alignment section 160, a cornea focusing section 180, and a retina focusing section 192. An optional display 260, such as a conventional type of CRT or LC display monitor, for example, can be used to display images obtained from sensor 146 or cornea camera 170. This would be helpful, for example, for someone other than the patient to observe images obtained at different stages of focus or imaging operation.

Operator Steps for Imaging

In order to better understand the apparatus and method of the present invention, it is instructive to briefly summarize the sequence of operator procedures used for obtaining a retinal image with conventional fundus imaging cameras. An outline of these basic procedures is as follows:

1. Position the patient at the imaging apparatus. For most devices, a chin rest, forehead support, and other features are provided to help get the patient into position for imaging.
2. Make initial settings. This step may vary significantly from one manufacturer's camera to the next. Initial settings may include filter placement in or out of the optical path or selection of suitable focus lenses based on the state of the patient's vision (for a high degree of nearsightedness, for example). Brightness settings may also be made, based on patient age or other characteristics.
3. Center the pupil in the object field of the camera. This step requires x-y coordinate positioning the camera so that the patient's pupil is centered. With some types of fundus imaging devices, the operator performs this adjustment using a computer mouse, joystick or similar control to achieve pupil centering. For a conventional fundus imaging device, FIGS. 8A and 8B show the arrangement of display screens on an operator interface display 138. A thumbnail, black and white image 250 of eye E appears, as shown in FIG. 8A. The operator uses the mouse, joystick, or other suitable pointing mechanism to manipulate the position of a cursor 261, centering it within the image of the pupil in image 250. Motion control logic in fundus imaging appliance 220 responds by aligning eye E with the optical axis of the apparatus. The operator can further "fine-tune" the alignment adjustment using any of various command entry tools to achieve a pupil-aligned image 252, as shown in FIG. 8B. With this procedure, the operator is ready to obtain suitable alignment of the pupil with respect to the optical axis.
4. Achieve coarse focus of the retina. This may be obtained, for example, by sliding the camera body forward or backward. Typically, an infrared viewing source is used to guide focus operation. Various cameras display focus indicators to the operator, such as a pair of bright spots that overlap when approximate focus is achieved. As shown in FIG. 8C, the corneal image now becomes a thumbnail image 262 and a full-size image 254 provides a monochrome preview image on display 138.
5. Achieve fine focus of the retina. Fine focus is typically obtained by adjustment of optics within the imaging apparatus itself.
6. Capture the retinal image. The operator obtains the retinal image once fine focus of the retina is achieved. Typically, the operator instructs the patient to blink, then obtains the image a moment afterward, when the eye is again fixated along the axis.

The above sequence of steps is, in broad outline, the procedure used for an operator-assisted fundus imaging apparatus. The various models and types of fundus imaging cameras currently available may provide a number of different utilities to support each step in the process. For example, a number of these apparatus provide automated alignment and/or automated focusing. Even with these utilities, however, these devices still require some level of operator interaction. It can be appreciated that there would be particular advantages to a fully automated fundus imaging apparatus, not requiring operator intervention once the patient is identified to the system and is seated.

Automated Steps for Imaging

The present invention automates the sequence of steps outlined above in order to provide a fundus imaging apparatus that does not require operator interaction. Once the patient is seated or otherwise positioned with the eye to be imaged placed reasonably close to the objective lens, the automated camera of the present invention is capable of executing steps that heretofore were performed by an operator. The patient must perform a small number of steps in order to facilitate alignment and focusing as well as to indicate readiness for imaging, as described subsequently.

Figure 7:
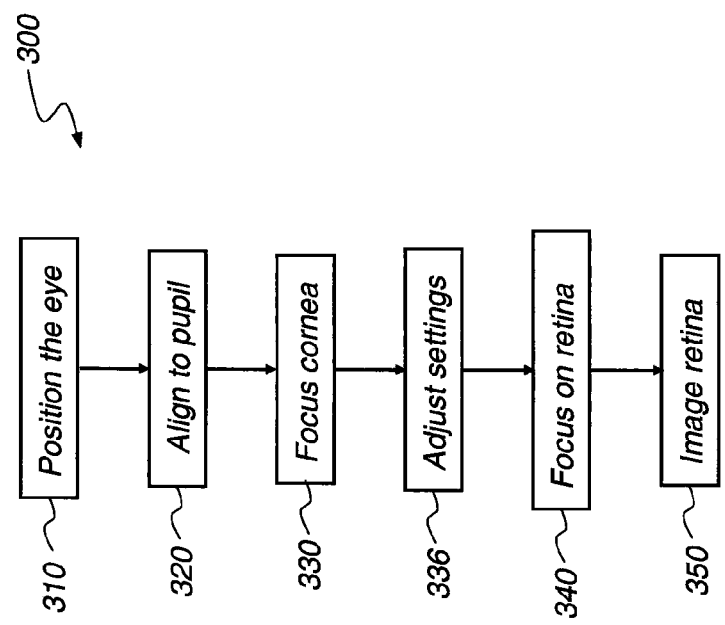
FIG. 7 is a process flow diagram showing the basic steps used for obtaining a retinal image using the imaging system of the present invention.

Referring to FIG. 7, there is shown a flow diagram of the steps as performed by automated fundus imaging appliance 220 of the present invention as shown in FIG. 6. In an automated imaging sequence 300, an initial step is a patient positioning step 310. Fundus imaging appliance 220 of the present invention may assist the patient with a visual or verbal instruction to look into the device with the right or left eye. An optional indicator element 410 is an input device of some type that, in one embodiment, can detect the presence of the patient near or at the device. Indicator element 410 could include any of a number of types of sensing devices that require no direct interaction from the patient. Alternately, in one embodiment, indicator element 410 could be a switch that is located on or near the camera, operated by the patient to initiate operation or to otherwise indicate readiness for imaging. Or, in a kiosk arrangement or other arrangement that allows patient selection of a type of test, the function of indicator element 410 could be performed by a touchpad screen or menu selection as possible input devices, for example. At a minimum, the function of indicator element is to indicate to automated fundus imaging appliance 220 that the patient:

(i) is in proper position, that is, in position to see the required target; and (ii) is ready to proceed with image capture.

An alignment step 320 is then initiated once the patient is in position. Alignment step 320 is carried out automatically, using positioning techniques and methods such as those described in U.S. Pat. No. 6,733,129. In alignment step 320, control logic processor 214, using image detection algorithms as known in the image processing arts, senses the position of the patient's pupil based on the image detected at cornea camera 170. The patient may need to indicate that the target is in view, such as using a switch 416 or other input. Alternately, eye motion algorithms could be used to automatically ascertain patient fixation on the target. Based on the position of the pupil that is sensed, control logic processor 214 sends commands to motor assembly 408, which acts as an alignment actuator to adjust the position of optical components until a suitable alignment positioning is achieved. Control logic processor 214 continues to monitor this alignment throughout subsequent steps, making adjustments as necessary. A cornea focusing step 330 follows, during which the cornea is brought into focus for cornea camera 170.

In an adjust settings step 336, control logic processor 214 makes a number of additional adjustments based on the image detected at cornea camera 170. For example, information such as relative pupil size and color characteristics of the eye can be used to set illumination levels for the patient.

A focus step 340 follows, during which a suitable retinal focus is achieved. For this step, control logic processor 214 causes the eye to be illuminated and detects the image feedback from sensor 146. Based on the focus detection, control logic processor 214 sends commands to a focus motor 406 that, acting as a type of focusing actuator, adjusts the focus position of lenses 144 and 251. Following this, imaging algorithms are used to determine focus, as is described subsequently. Control logic processor 214 may continue to check and monitor focus as necessary.

Once focus is achieved, an image capture step 350 can be executed. Control logic processor 214 may instruct the patient to blink or may detect a blink event, then capture the retinal image at a suitable moment following this event.

There are a number of options available for executing the steps of automated imaging sequence 300. For example, numerous types of image detection algorithms exist, enabling control logic processor to sense proper imaging conditions from cornea camera 170 and sensor 146 in a number of ways. In place of indicator element 410, the patient could even be provided with a control that enables the image to be taken when setup, alignment, and focus are achieved and the patient is ready. That is, using a camera analogy, the patient could be provided with shutter control to actually capture the image at the patient's command. However, image capture would be enabled only when conditions of alignment and focus are deemed suitable. There are a number of types of focus detection mechanisms that could be employed for automated focus detection and response.

Pupil tracking and pupil sizing algorithms could also be used in conjunction with fundus imaging appliance 220, in order to make necessary adjustments for alignment and focus. Image data obtained from camera 170, refreshed at a suitable rate for pupil tracking, is analyzed using any of a number of suitable algorithms for pupil tracking, such as any of the following, for example:

(i) center of mass calculation that determines the center of the pupil opening and uses a fixed or adjustable diameter as a pupil shape;

(ii) threshold evaluation that automatically determines a threshold source image value representing pupil area and uses that threshold to trace out the pupil outline; this method could alternately use a median filter for smoothing;

(iii) threshold evaluation combined with a connected components analysis that identifies the pixel area;

(iv) threshold evaluation that locates the center and bounding box of the pupil region; or (v) center of shape detection algorithms.

Fundus imaging appliance 220 executes the basic steps shown in FIG. 7 automatically, with the option of patient involvement in one or more steps. Once the pupil size is detected, the optimal size of light ring 40 (FIG. 5) can be determined and a suitable light ring 40 provided, such as with a selection of apertures 412 and 414 in illumination section 112 (FIG. 6). A liquid crystal light modulator could be used in the illumination path for programmable aperture sizing.

Eye Alignment

Figure 9A:
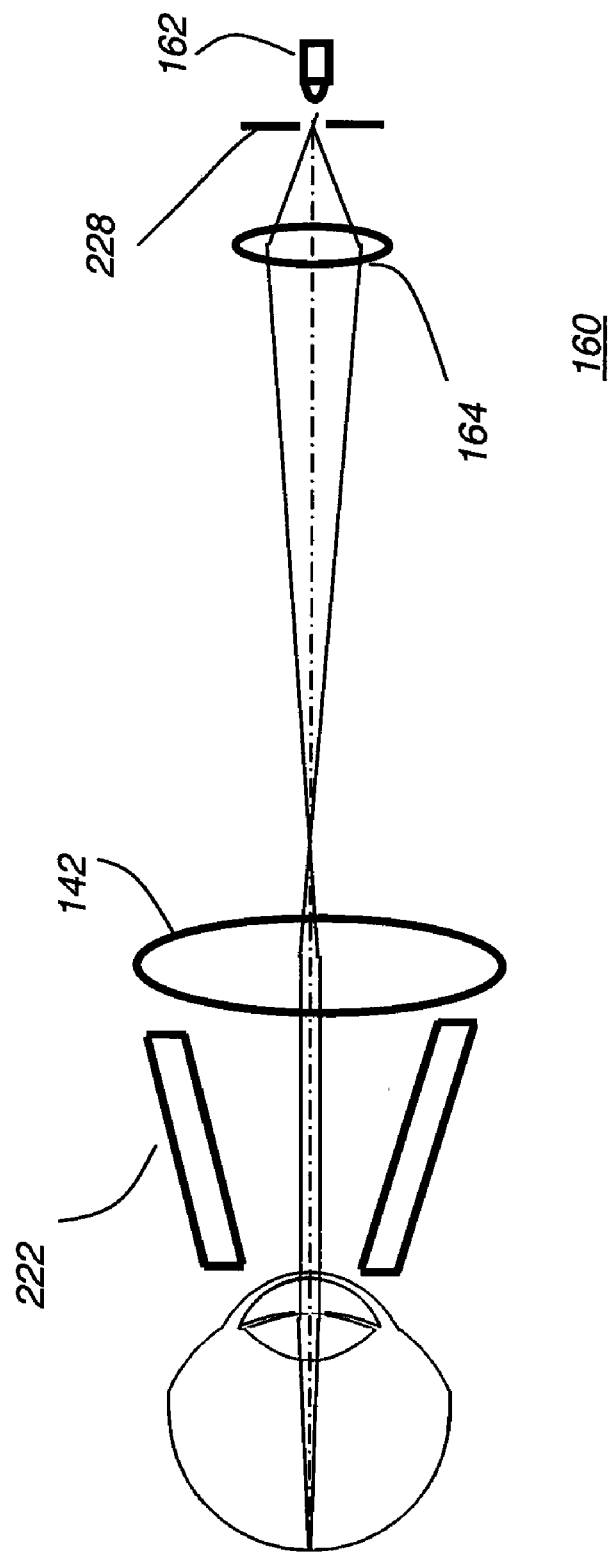
FIG. 9A is a schematic block diagram showing alignment apparatus according to one embodiment.

Alignment section 160 provides aiming and accommodation of the patient's vision, in order to position the eye E favorably for fundus imaging in alignment step 320 of FIG. 7. Alignment section 160 is shown in simplified form in FIG. 9A. The patient's eye is coarsely positioned by being placed against an eye holder 222 or a chin rest. An aiming target aperture 228 with an aiming target light source 162, such as an LED or other visible light source, is visible to the patient through beamsplitters 224 and 172, mirror 174, and a movable polarization beamsplitter 226 (FIG. 6), providing collimated light.

In FIG. 6, light source 162 is shown at one of its possible positions. As the simplified block diagram of FIG. 9A suggests, light source 162 can be disposed at any suitable position along the optical path. The beam diameter in one embodiment is about 5 mm. The collimated light is used to orient the eye of the patient to a position that provides visual accommodation. That is, when the patient views aiming target aperture 228 through lens 142 and a lens assembly 164, the light entering eye E is substantially collimated. Relative to the coordinate axes shown in FIG. 6, the alignment procedure along optical axis $O_a$ sets the position of eye E along the z axis, and provides alignment positioning relative to the orthogonal x and y axes.

For a patient operated system, the patient can indicate that the target is clearly visible, using a switch or other mechanism. This indicates that alignment is achieved and cornea centering and focus can be initiated.

Cornea Centering and Focus

Figure 9B:
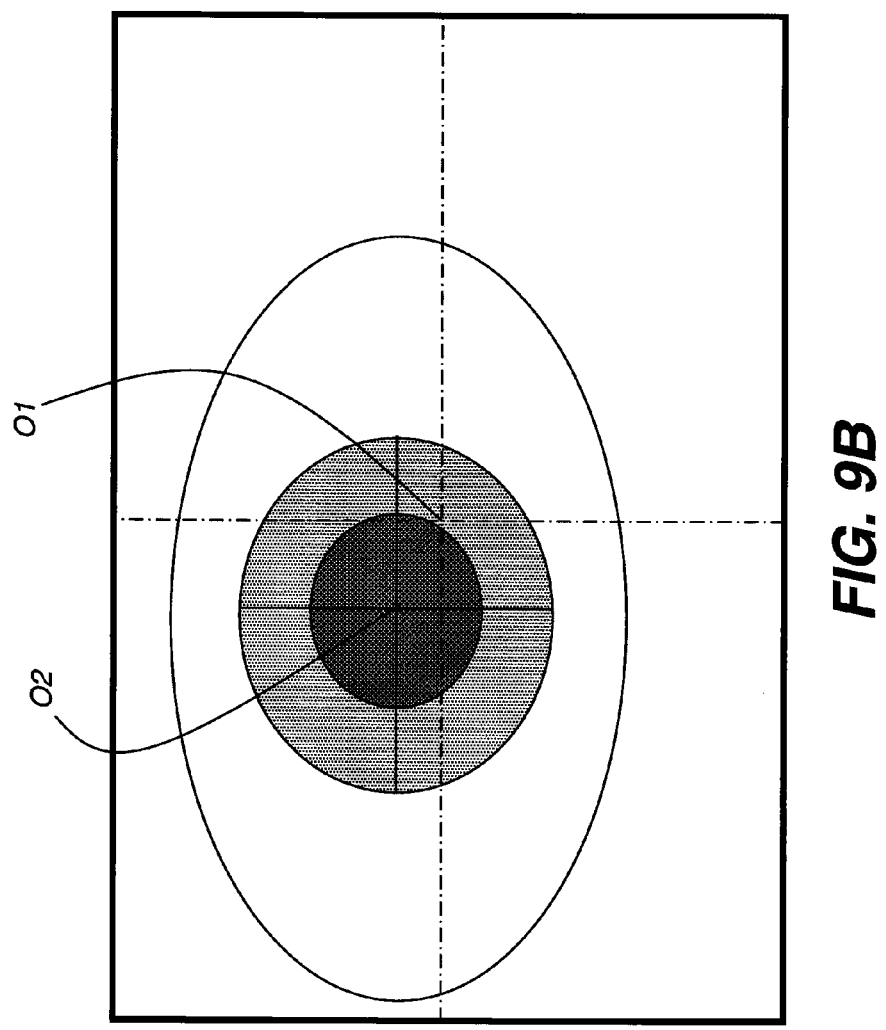
FIG. 9B is a plan view showing an arrangement of illumination rings used for cornea focus.

Once alignment of eye E is achieved, centering of the cornea relative to optical axis O is necessary. Referring to FIG. 9B, the principle of centering is shown. The center of the iris or pupil O1 can be determined using image analysis software and can be compared with the center O2 along the optical axis of a camera.

When necessary to center the cornea, pupil profiling light sources 176, near-IR sources in one embodiment, are first turned on to provide peripheral illumination to the cornea. The reflected light is then directed, through beamsplitters 172 and 166 and through lens or lens assembly 168, to cornea camera 170, which is optically conjugate to the cornea. Cornea camera 170 can be a relatively inexpensive imaging device, requiring only that it have sufficient resolution for focusing. In one embodiment, for example, cornea camera 170 is a CCD camera, model no. IK-52V manufactured by Toshiba.

Once the image signal about the cornea is obtained, image analysis software in control logic processor 214 assesses the cornea centering, as described with reference to FIG. 9B, and adjusts the x and y position of optical assembly components by controlling a motor assembly 408 which serves as an actuator for obtaining alignment.

Figure 10A:
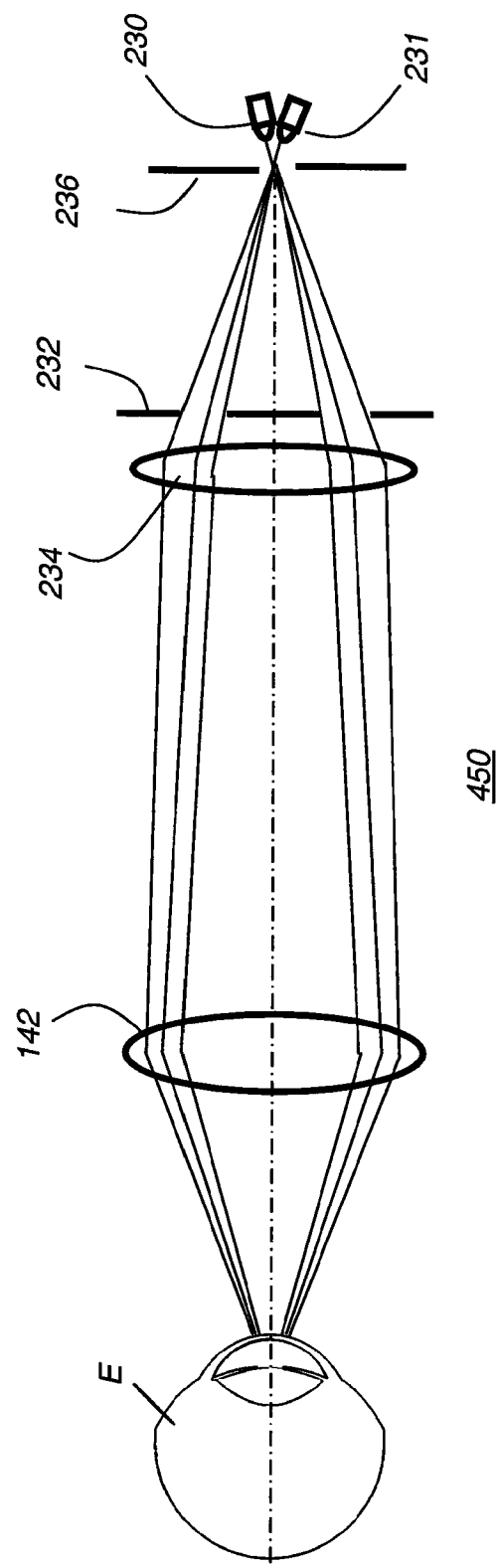
FIGS. 10A, 10B, and 10C are side view block diagrams showing cornea focus in one embodiment.
Figure 10B:
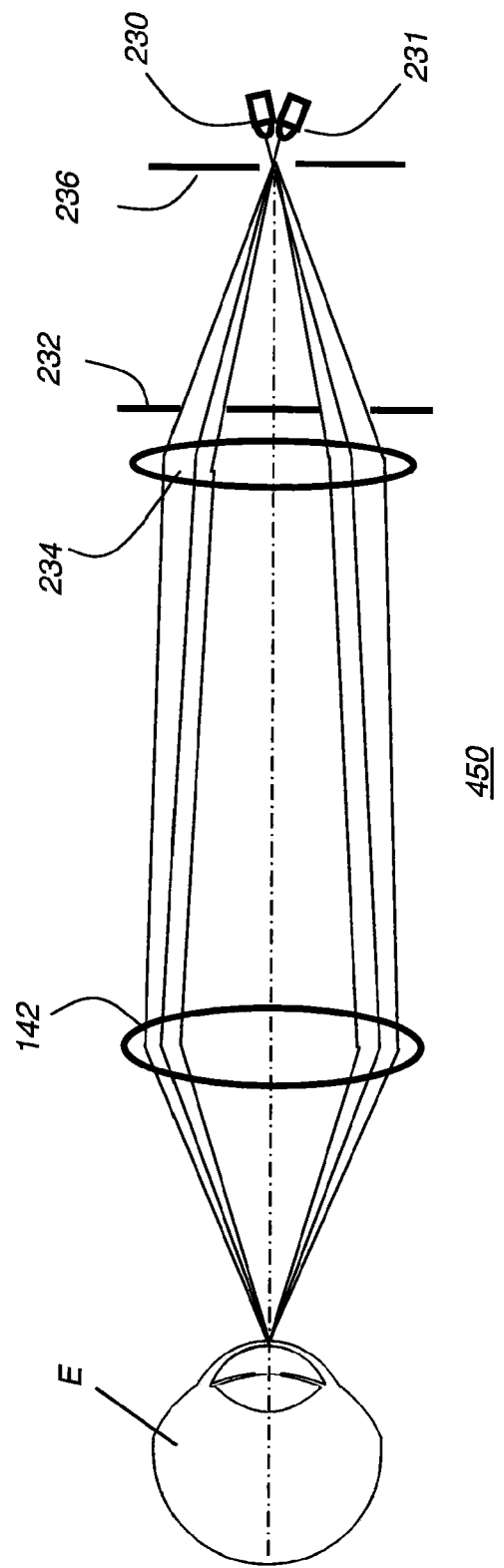
Figure 10C:
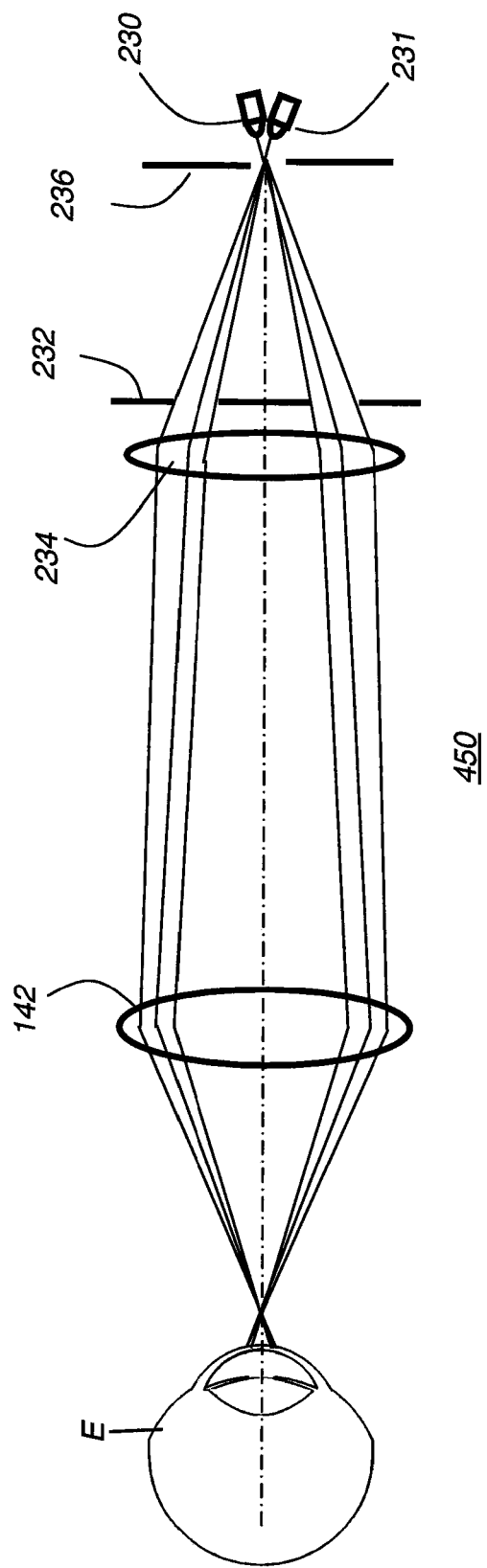

Following centering, focus cornea step 330 of FIG. 7 can be executed. For cornea focus, optical components must be adjusted in the z direction. To focus the cornea once it is centered, pupil profiling light sources 176 are then switched off and light sources 230 and 231 are alternately switched on and off. Light from light sources 230 and 231 goes through apertures 236 and 232 that are configured to provide the light for each focus indicator. Light sources 230 and 231 are oriented so that the optical axes along which their light is directed are not overlapping. Both light sources 230 and 231 point toward their respective openings in aperture 232. A mechanical shuttering mechanism (not shown) could alternately be used to alternate the light from light sources 230 and 231 instead of switching them alternately on and off. A lens 234 operates to image aperture 236 onto the cornea. FIGS. 10A, 10B, 10C, and 11 show how cornea focus is determined using a cornea focus detection section 450. FIG. 11 shows the appearance of images 236a' and 236b' of aperture 236 in a field 171 of cornea camera 170, as images 236a' and 236b' would appear when the cornea is not in focus, such as in the positions of FIGS. 10A and 10C, for example. When the cornea is in focus, as shown in FIG. 10B, overlap occurs so that only a single image 236a' and 236b' is visible. Control logic processor 214 employs an imaging algorithm to determine whether there are two images 236a' and 236b' or a single image with image 236a' overlapping 236b'. Based on the relative position and movement of images 236a' and 236b' with respect to each other, control logic processor 214 then controls motor assembly 408 appropriately to adjust the cornea focus. This requires movement of sensor 146 and related components according to the movement of images 236a' and 236b'.

Retinal Focus

Figure 12A:
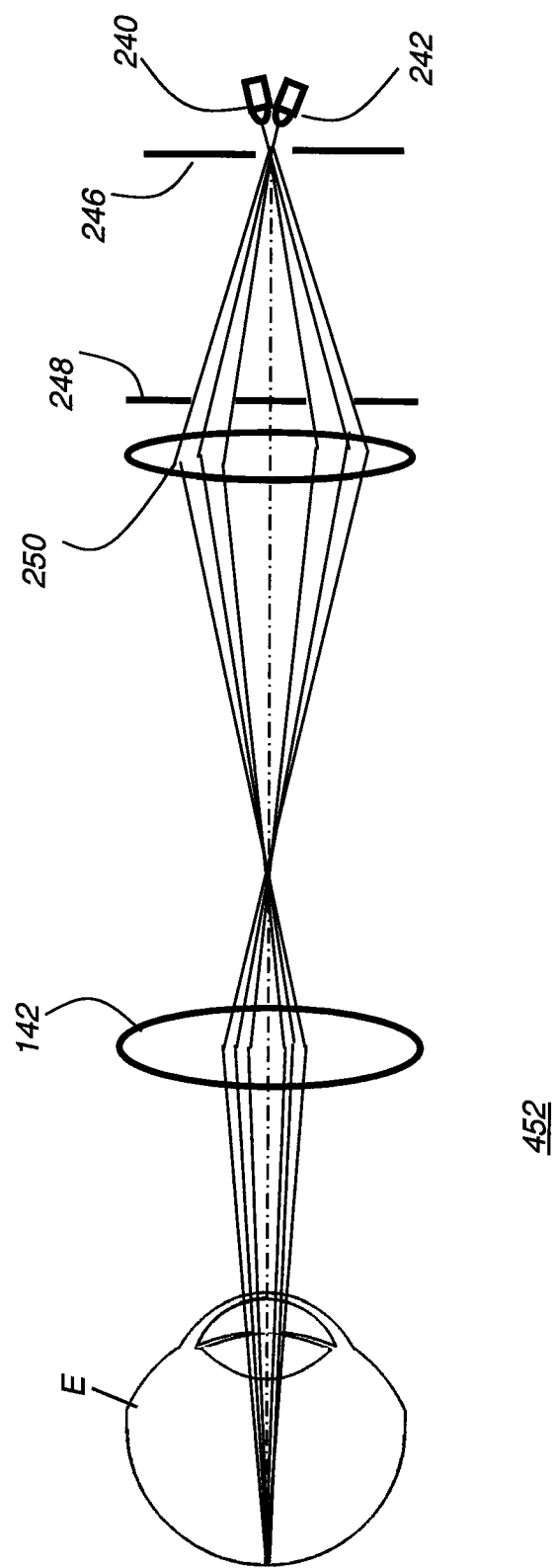
FIGS. 12A, 12B, and 12C are side view block diagrams showing retina focus in one embodiment.
Figure 12B:
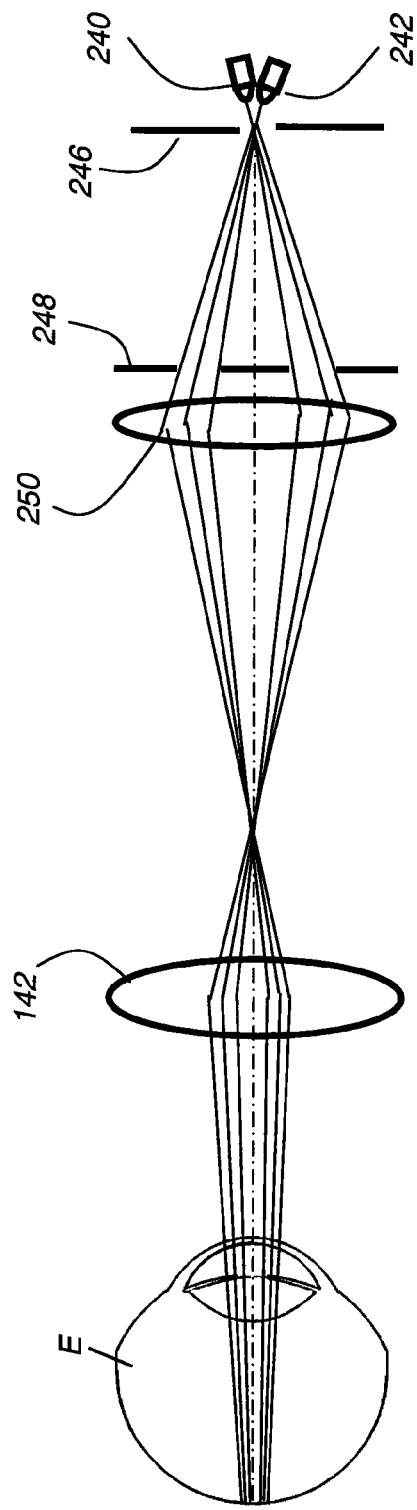
Figure 12C:
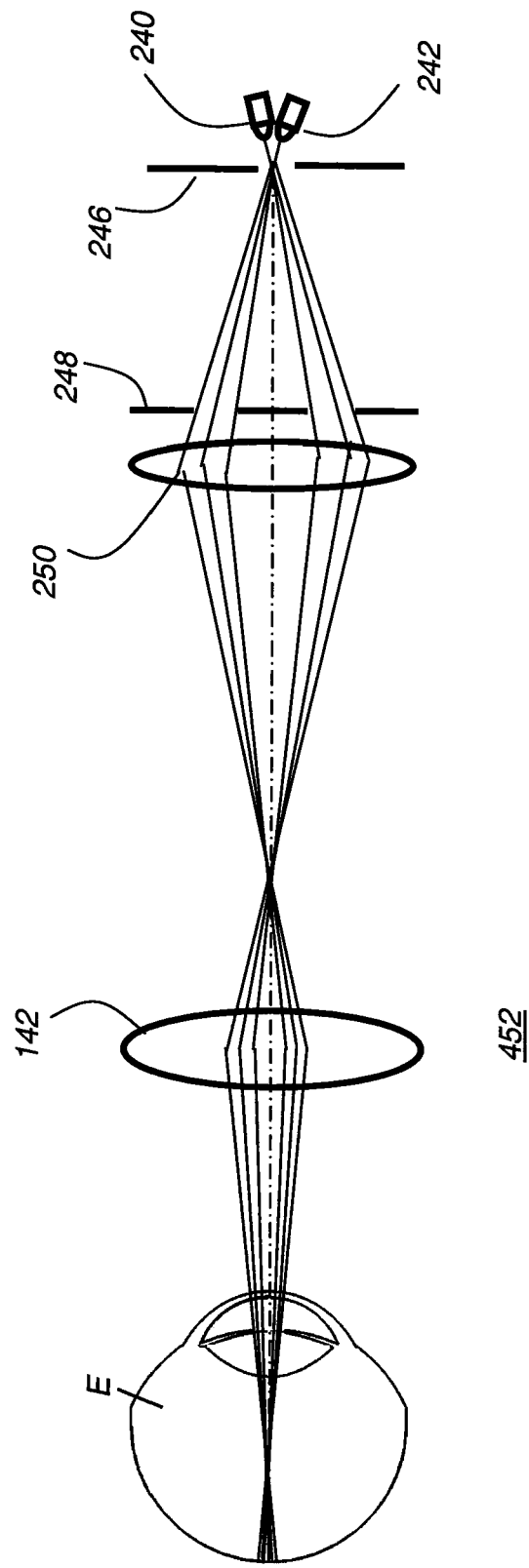

Once cornea centering and focus is achieved, retinal focus can be obtained automatically using focus step 340 (FIG. 7) of the apparatus of the present invention. To obtain retinal focus, images of an aperture are also used as feedback control signals, with a sequence similar to that followed for cornea focus. Referring to FIGS. 12A, 12B, and 12C, components of a retina focus detection section 452 of fundus imaging appliance 220 are shown. FIG. 12A shows the in-focus state. Light sources 240 and 242 are alternately switched on and off to image an aperture 246 onto the retina of the eye. Aperture 246 is imaged through an aperture 248 and lenses 250 and 142. Referring to FIG. 13, there is shown a sensor field 147 for sensor 146 that is used for retinal focus and imaging. Two separate images of aperture 246a' and 246b' appear in sensor field 147 during an out-of-focus condition. At focus (FIG. 12A), the two images of aperture 246a' and 246b' overlap. Based on the position and relative movement of images of aperture 246a' and 246b', control logic processor 214 controls a motor 406 to adjust the focus position of both lenses 144 and 251 (FIG. 6) in order to obtain focus.

Once retinal focus is achieved, fundus imaging apparatus may repeat any portion or all of the sequence described with reference to steps 320, 330, 336, and 340 in FIG. 7. Control logic processor 214 may continuously check for cornea focus, for example, at various intervals and may recheck retinal focus immediately prior to imaging.

Image Capture

Once proper conditions of alignment and focus have been obtained, control logic processor 214 enables an image of the retina to be obtained in image capture step 350 (FIG. 7). For this step, an image capture light source 114 is flashed on. Light from image capture light source 114 goes through a lens or lens assembly 178, an aperture 412, a lens 126, and an aperture 414 and is reflected onto the optical axis O by apertured mirror 28. Movable polarization beamsplitter 226 is shifted so that sensor 146 receives the retinal image.

The patient can be prompted to operate fundus imaging appliance 220. For example, the patient can operate an optional switch 416 that acts as a type of shutter. Pressing switch 416 instructs control logic processor 214 that the patient is ready for imaging. Control logic processor may not enable imaging until cornea and retinal focus is achieved, however. A message can be displayed that instructs the patient to blink so that the image can be obtained after a short delay. Aiming target aperture 228 could be a display device that also provides a short message in addition to providing the fixation target, for example. Allowing the patient to indicate readiness has psychological advantages for the patient, since it gives the patient some amount of control for apparatus function and helps to ready the patient for the bright flash that occurs during imaging.

Alternate Embodiments for Cornea Focus

Figure 14:
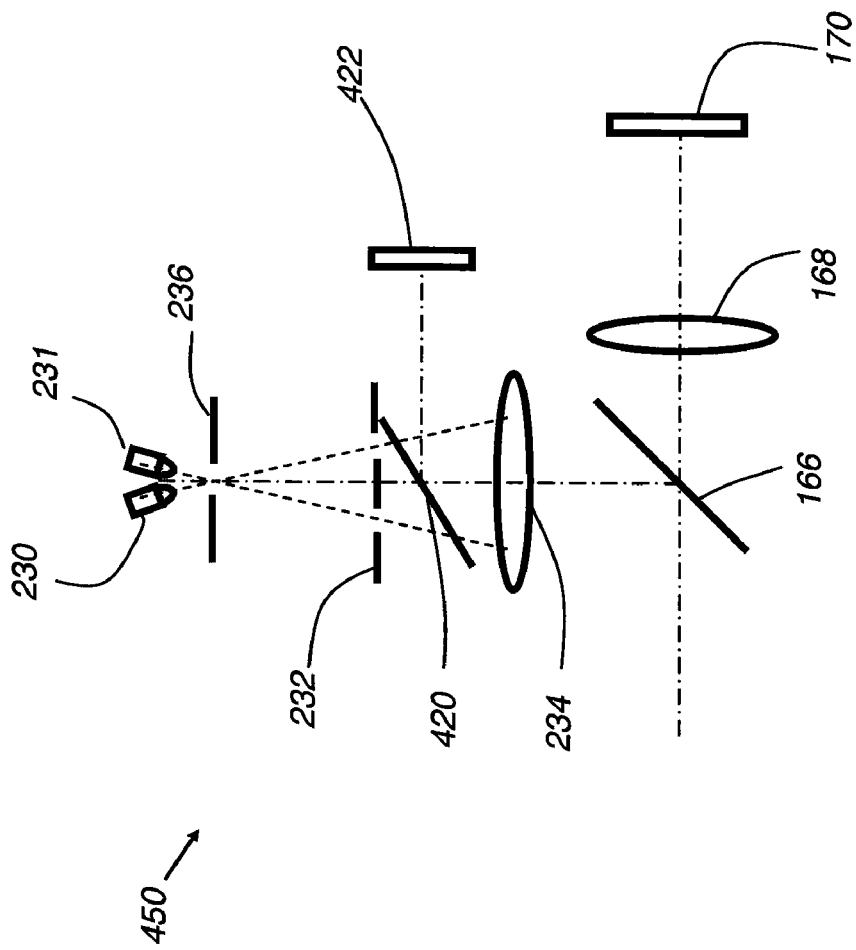
FIG. 14 is a schematic diagram showing how cornea focus is achieved in one embodiment.

Referring to FIG. 14, there is shown one alternate embodiment for cornea focus components. In this embodiment, a sensor 422, such as an inexpensive CCD or CMOS sensor, is positioned in the path provided by a beamsplitter 420 for sensing overlap of image of aperture 236a' and 236b' from the eye. This embodiment can be advantaged by providing separate sensing components for centering and focus.

Figure 15:
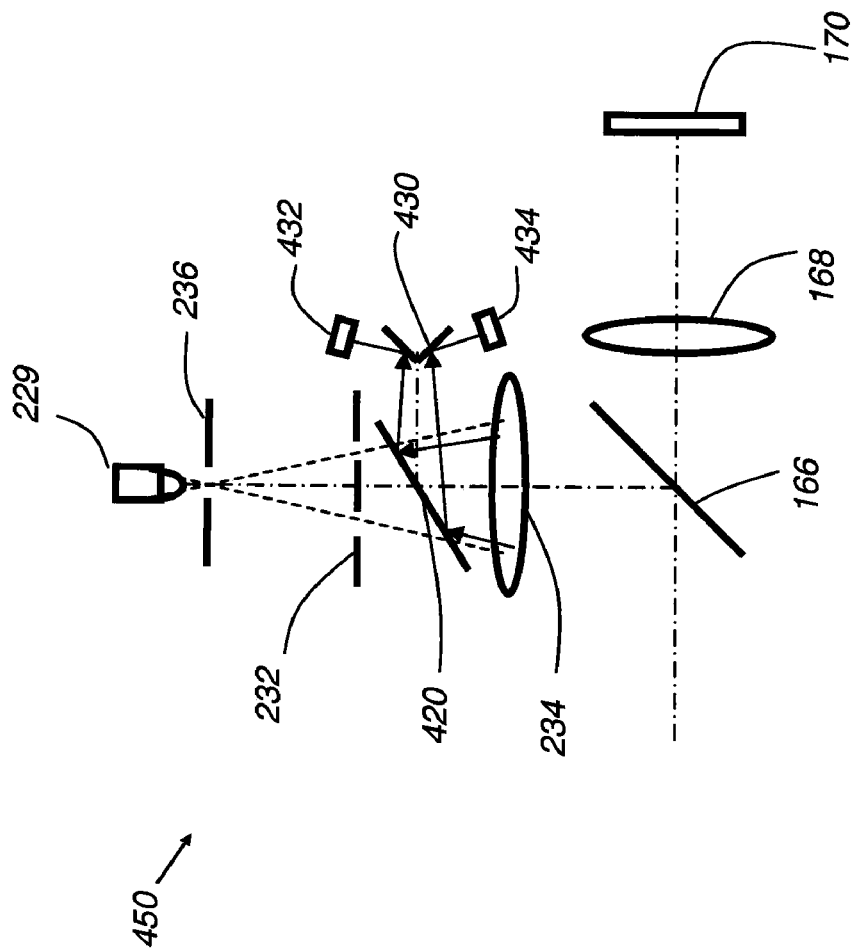
FIG. 15 is a schematic diagram showing how cornea focus is achieved in another embodiment.

Another alternate embodiment for cornea focus components is shown in FIG. 15. Here, only a single LED 229 is needed. Since there are two openings in the aperture 232, two bundles of light from the LED 229 reach the cornea surface and partially reflect back. Beamsplitter 420 provides reflected lights to a folding element 430 that sends two bundles of the reflected light to two sensor devices 432 and 434 separately. The light sensor devices 432, 434 can be inexpensive CMOS or CCD sensors, for example, or some other type of position sensitive device. As with the embodiment of FIG. 14, different sensors are used for centering and cornea focus with this arrangement.

Figure 22:
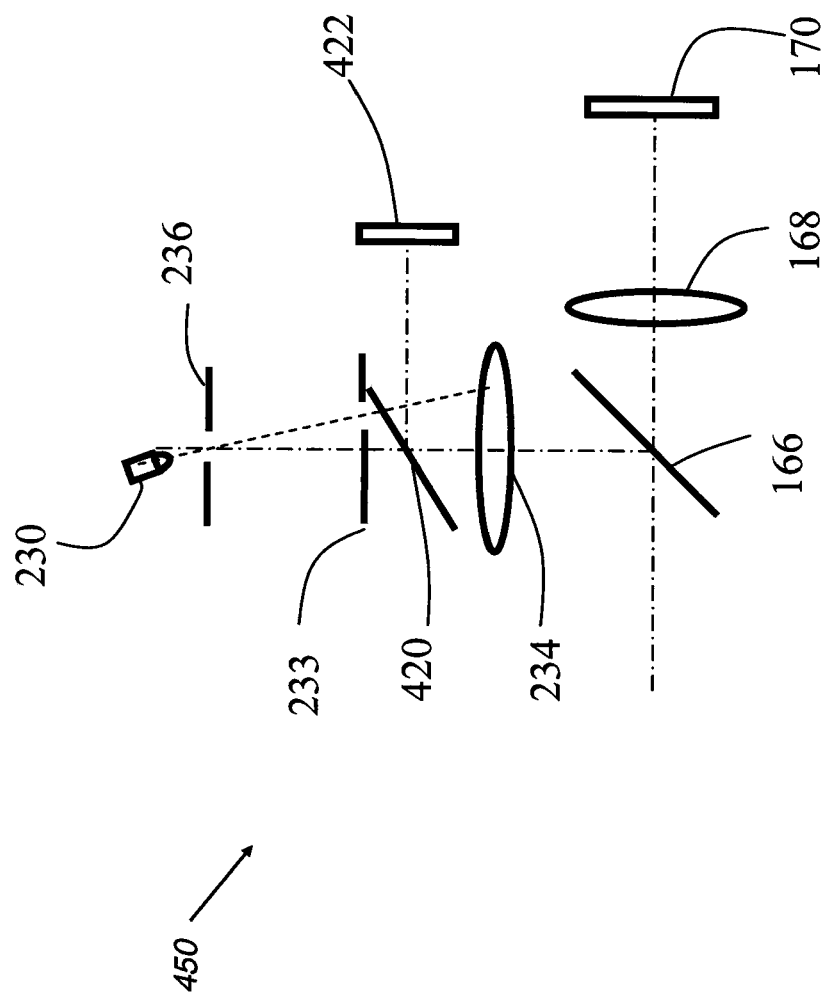
FIG. 22 is a schematic view of components for cornea focus in an alternate embodiment.

Yet another alternate embodiment for cornea focus detection section 450 is shown in FIG. 22. This embodiment uses a single light source 230 and a single sensor 422. A pinhole aperture 236 must be optically centered with respect to sensor 422, or in some other predefined position. Second aperture 233 requires only one opening rather than two with this embodiment. A beamsplitter 420 provides the illumination from light source 230 to a lens or lens assembly 234 and to another beamsplitter 166 that directs this illumination toward the cornea. Beamsplitter 166 directs the reflected image through a lens 168 and to a cornea camera 170 for focus assessment. When using only light source 230 and not two light sources as shown in other embodiments, there is no need for switching the illumination on and off. Good calibration is needed so that the detected image of pinhole aperture 236 is centered at sensor 422, or in some other predefined position with the cornea in focus.

Figure 23:
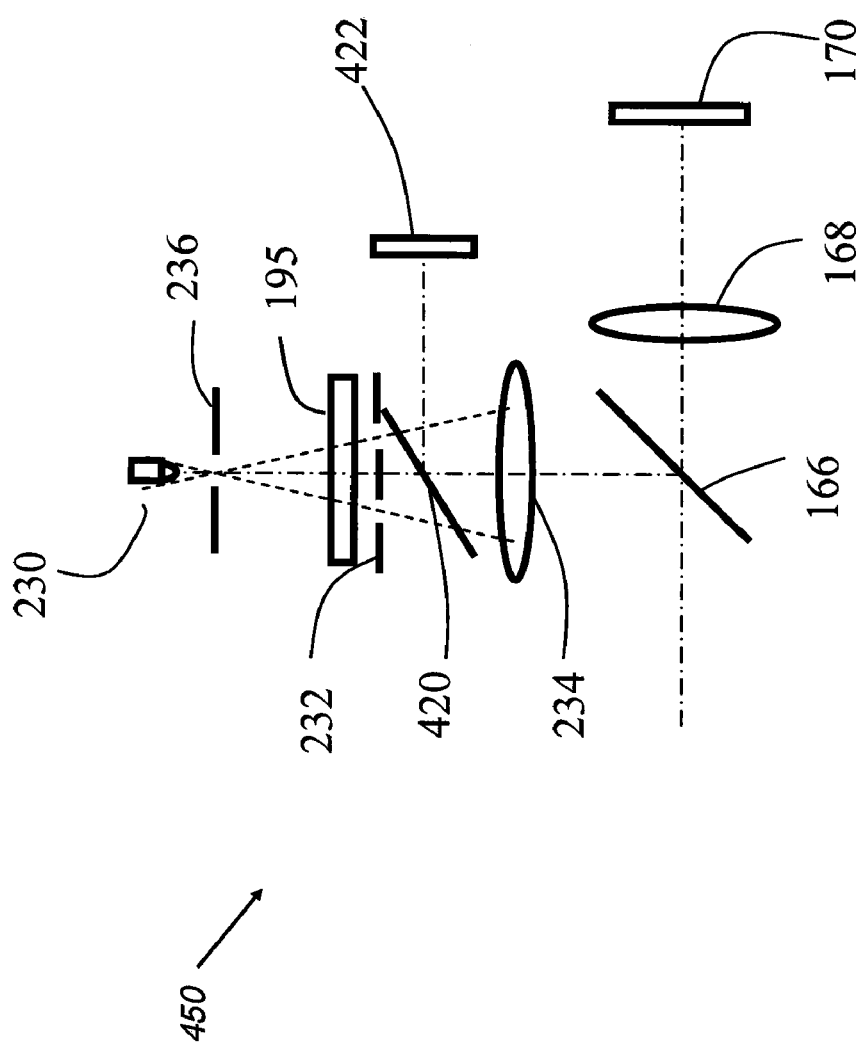
FIG. 23 is a schematic view of components for cornea focus in another alternate embodiment.

Yet another alternate embodiment for cornea focus is shown in FIG. 23. This embodiment adds a spatial light modulator 195, such as a transmissive liquid crystal (LC) device, or other type of electro-optical or electromechanical device employed as a type of shuttering mechanism. Spatial light modulator 195 is used to alternate light from light source 230 to different openings in aperture 232. When spatial light modulator 195 is energized, only one opening in aperture 232 receives light at a time. Two images of aperture 236 are received on camera 170, in an alternating sequence.

Alternate Embodiment for Retinal Focus

Figure 16:
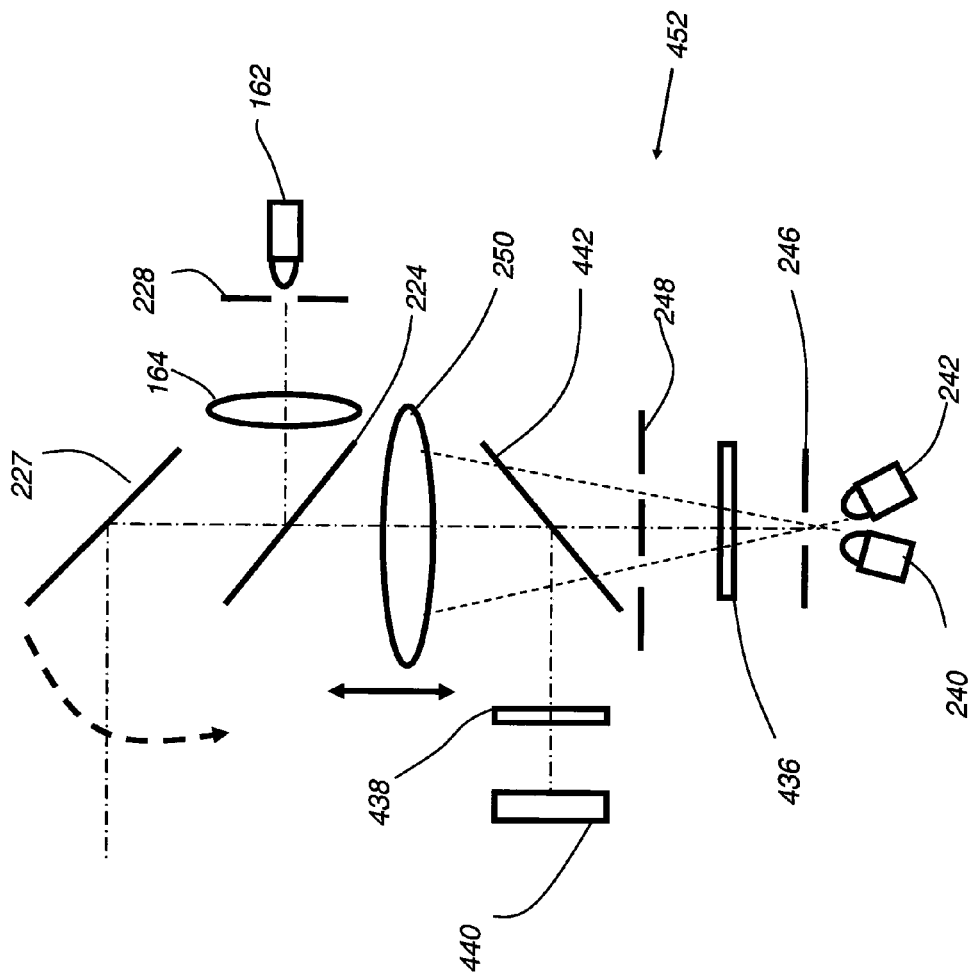
FIG. 16 is a schematic diagram showing how retinal focus can be obtained in one embodiment.

Referring to FIG. 16, there is shown an alternate embodiment for obtaining retinal focus. An auxiliary sensor 440 obtains, through a beamsplitter 442, images of aperture 246*a'* and 246*b'* as was described with reference to FIG. 13. Auxiliary sensor 440 may be an inexpensive sensor, such as a CCD or CMOS device or some other light-position sensing component. A polarizer 436 polarizes the light that is alternately emitted from light sources 240, 242. An analyzer 438 is positioned in front of auxiliary sensor 440 and is oriented with its transmission axis orthogonal to that of polarizer 436 in order to block reflected light from the lens surfaces and cornea of the eye. Light sources 240, 242 are oriented to direct light through portions of aperture 248 and arranged so that two bundles of light do not overlap. This creates a cross-talk free condition for the light from light sources 240 and 242. A movable mirror 227 enables these components to be switched into the optical path when needed. With this embodiment, retina focus can be obtained quickly, without the need to employ a higher-resolution imaging sensor 146.

Figure 17:
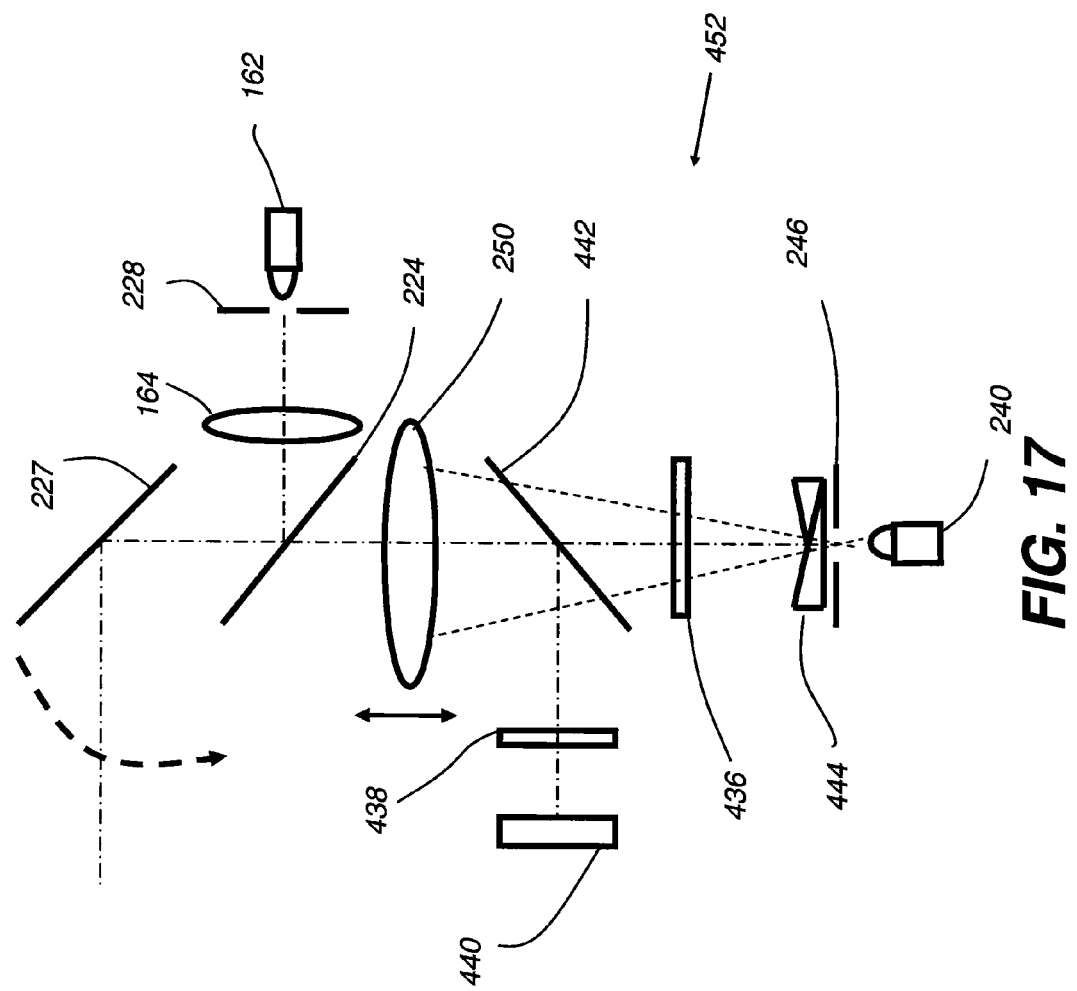
FIG. 17 is a schematic diagram showing how retinal focus can be obtained in an alternate embodiment.
Figure 18:
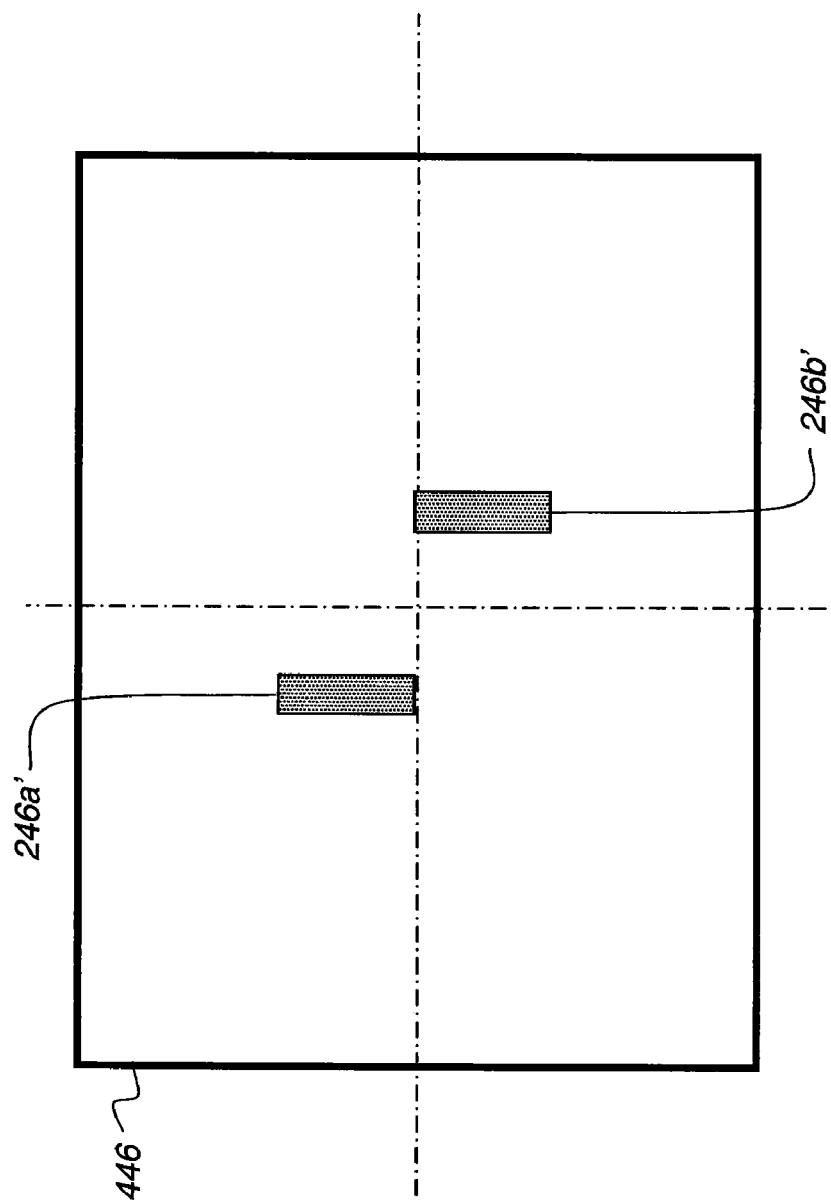
FIG. 18 is a plan view of the sensor field for a retina out-of-focus condition in one embodiment.
Figure 19:
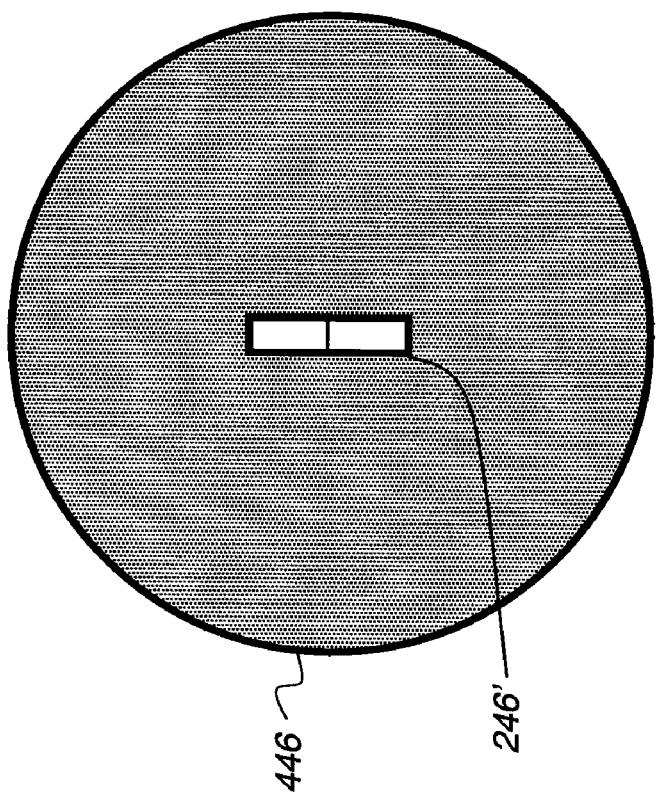
FIG. 19 is a plan view of the sensor field for the retina in-focus condition in one embodiment.

Referring to FIG. 17, there is shown another alternate embodiment for obtaining retinal focus. Here, a single light source 240 is used, emitting light that is polarized by polarizer 436. Analyzer 438 is positioned in front of auxiliary sensor 440 and has its transmission axis perpendicular to that of polarizer 436. A prism pair 444 generates two illumination beams from light source 240. The lights exiting from the prism pair 444 point to different directions and do not overlap. FIG. 18 shows a sensor field 446 during an out-of-focus condition of the retina; here, there are two images of aperture 246*a'* and 246*b'* that display. When the retina is in focus, images of aperture 246*a'* and 246*b'* overlap, as shown in the plan view of FIG. 19. The embodiment of FIG. 17 has the speed and cost advantages described with reference to the embodiment of FIG. 16 and requires one fewer light source.

Figure 20:
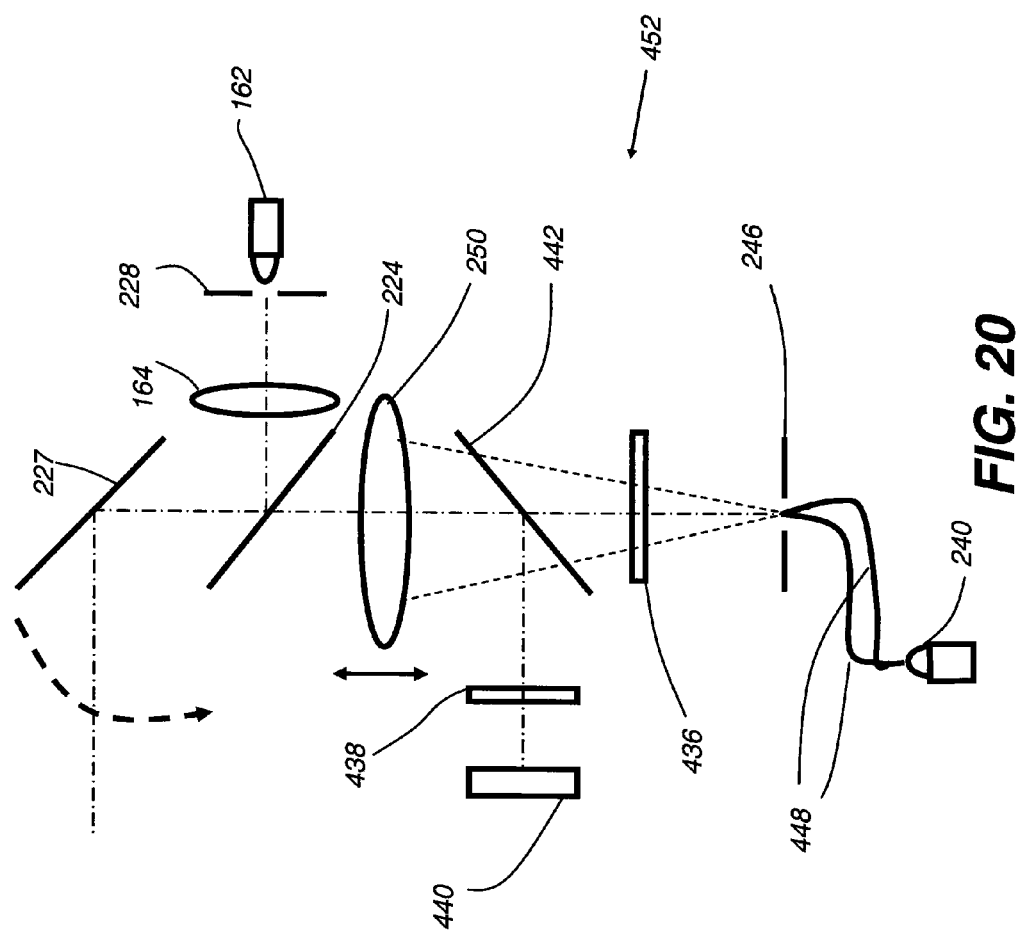
FIG. 20 is a schematic diagram showing how retinal focus can be obtained in an alternate embodiment.
Figure 21:
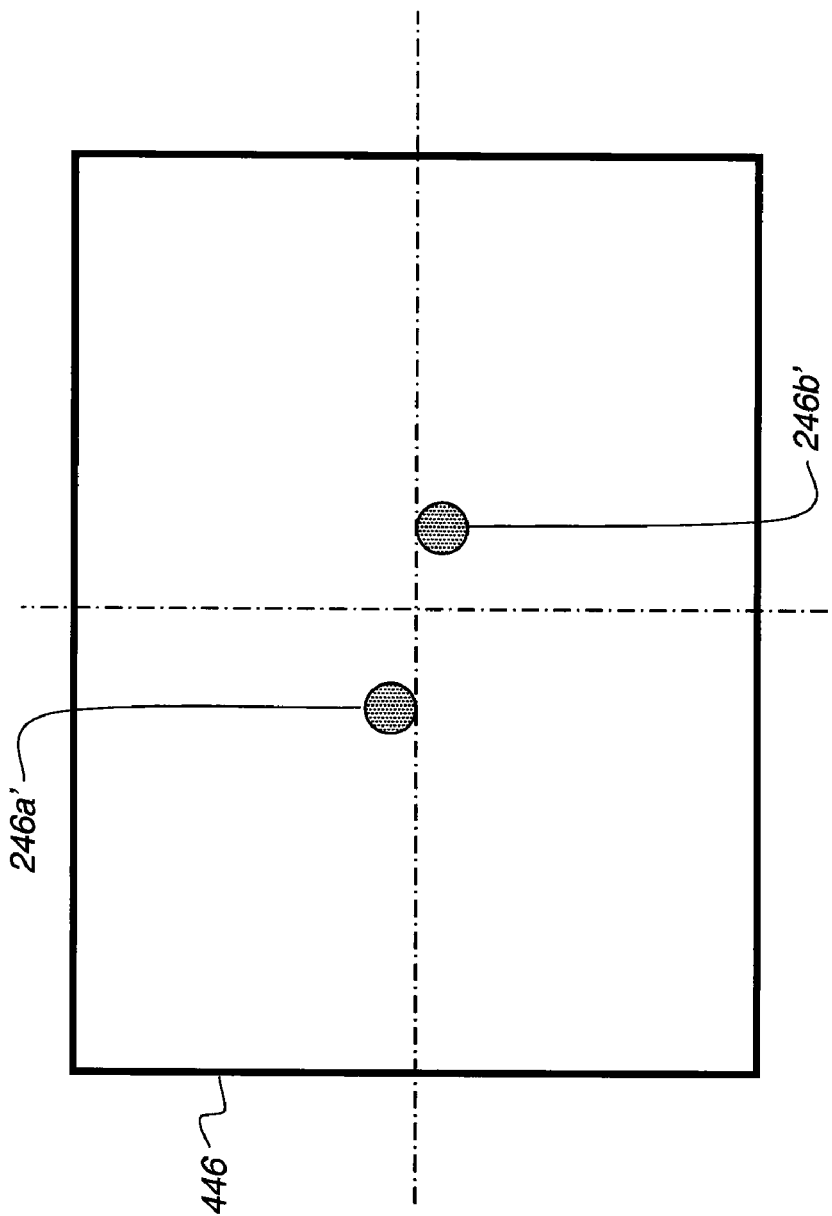
FIG. 21 is a plan view showing the sensor field for a retina out-of-focus condition in the embodiment of FIG. 20.

Referring to FIG. 20, there is shown yet another embodiment for retinal focus. Here, a pair of light sources is formed by directing light from light source 240 into two optical fibers 448. The lights exiting from the fibers point to different directions and do not overlap. Referring to FIG. 21, there is shown the arrangement of images formed from on sensor field 446 from the pair of optical fibers 448 using the embodiment of FIG. 20.

Figure 24:
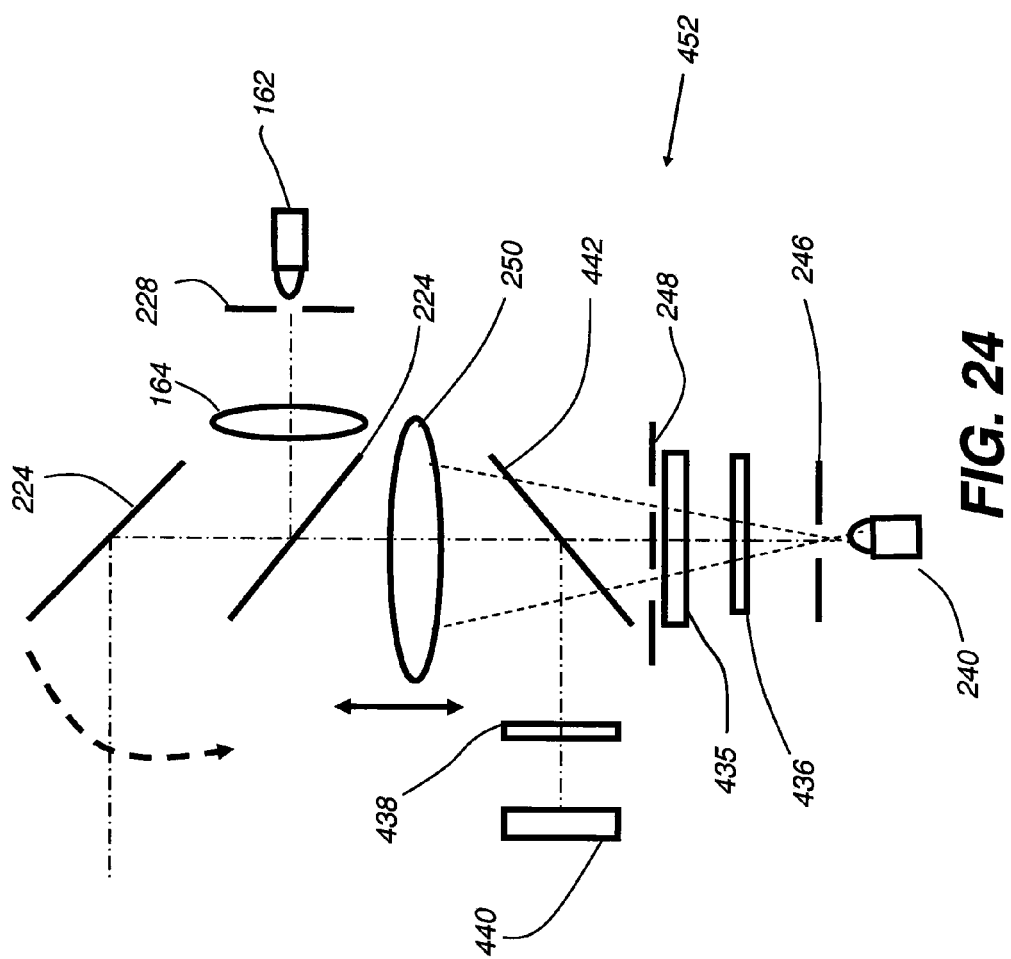
FIG. 24 is a schematic view of components for retinal focus in an alternate embodiment.

Referring to FIG. 24, there is shown yet another embodiment for retinal focus. A spatial light modulator 435, such as a transmissive LC device, is positioned as a shuttering mechanism for alternating the light from light source 240 through different portions of aperture 248. Alternate components could be used to provide this same shuttering action. With this embodiment, only one hole in aperture 248 provides light at one time. Sensor 440 detects two images of aperture 246 at separate times. Thus, this arrangement senses focus in a manner similar to embodiments using multiple light sources.

Sensing the Patient

In order to operate in a highly automated fashion, fundus imaging apparatus 220 of the present invention may have some way to detect that the patient has approached to a point near the device. Various types of indicator elements 410 could be used to detect the proximity of a patient, including detectors and sensors from Sick Incorporated, Minneapolis, Minn., for example. An optional camera could also be used, supported by image processing software that detects the image of a person. The presence of the patient may be used, for example, as part of an energy-saving system, to initiate full power-up from a "power-save" state of fundus imaging apparatus 220 in readiness for performing the setup and imaging operations described with reference to FIG. 7.

Unlike conventional fundus imaging devices currently in use, the apparatus of the present invention is advantaged in its capability to obtain retinal images in an automated fashion, requiring no interaction or intervention by an operator. This also makes fundus imaging appliance 220 suitable for self-use by a patient. Fundus imaging appliance 220 can be installed in a PCP office or lab facility, or could even be installed in a kiosk enclosure or other environment outside of a conventional medical setting. Where instructions might be helpful or necessary, fundus imaging apparatus 220 may display instructions to the patient or may provide audible instructions using optional speakers, for example.

The present invention provides a fundus imaging apparatus that requires no operator, allows compact packaging, and may not require dilation of the pupil for most patients. It must be emphasized that fundus imaging appliance 220, as described in the present application, is primarily intended to provide basic fundus imaging that can be inexpensively performed at the office of a PCP or other non-specialist site. Thus, more advanced imaging features and functions are omitted from this description of fundus imaging appliance 220. However, the same components and methods for automating setup and focus functions could also be applied to a more sophisticated imaging device.

Figure 25:
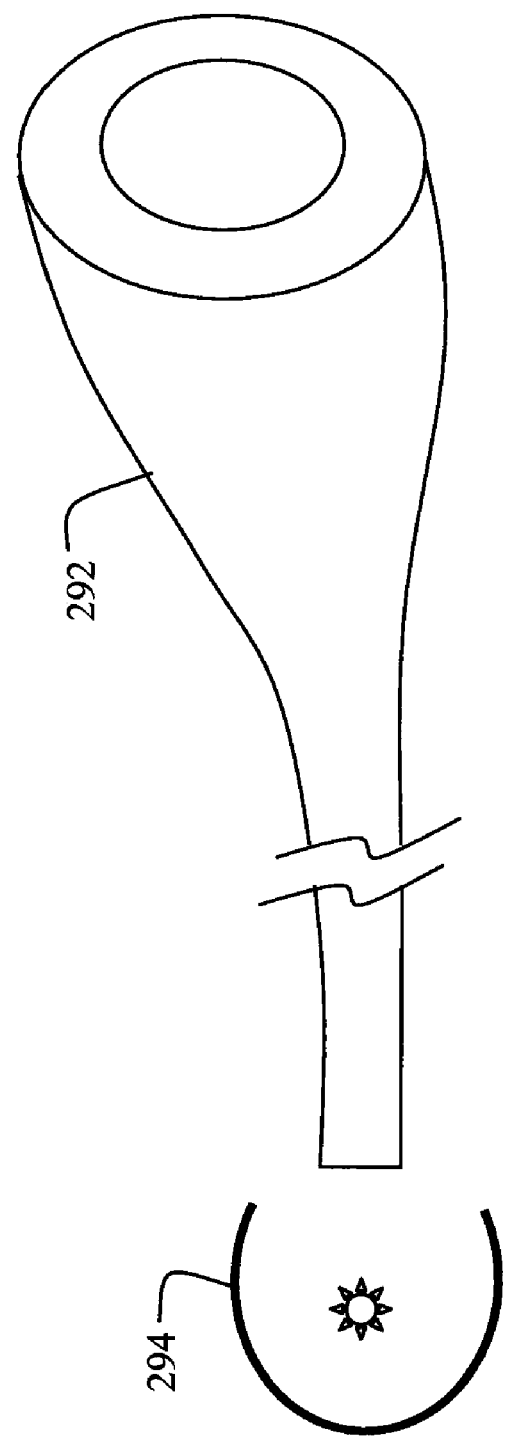
FIG. 25 is a block diagram showing a fiber-optic illumination ring in one embodiment.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, the various light sources used within fundus imaging appliance 220 allow a number of optional types. Sensors and CCD devices could be any of a number of different types. Referring to FIG. 25, an alternate embodiment for illumination directs light from a light source 294 through a fiber optic ring 292. This type of arrangement could be beneficial for optimizing illumination brightness and direction.

Although the resolution and overall image quality requirements for cornea camera 170 and sensor 146 are quite different, a single CCD array could be used for both cornea camera 170 and sensor 146, switched between these functions, using techniques well known in the imaging arts. Various types of reference locators could be used for assisting in the initial positioning of the patient. The patient is preferably seated; however, imaging could be obtained from a patient in some other position.

Thus, what is provided is an apparatus and method for automated fundus imaging.

PARTS LIST

10 fundus imaging apparatus
12 illumination section
14 observation light source
16 lens
18 image capture light source
20 lens
22 half-mirror
24 ring-slit diaphragm
26 lens
28 apertured mirror
30 inner ring
32 middle section 34 outer section
36 pupil
40 ring
46 sensor
100 fundus imaging system
102 image capture section
104 control logic processor
112 illumination section
114 image capture light source
126 lens
138 display
142 lens
144 lens
146 sensor
147 sensor field
160 alignment section
162 aiming target light source
164 lens assembly
166 beamsplitter
168 lens
170 cornea camera
171 field
172 beamsplitter
174 mirror
176 light source
178 lens
180 cornea focusing section
192 retina focusing section
195 spatial light modulator
210 control workstation
212 keyboard
214 control logic processor
216 network
220 fundus imaging appliance
222 eye holder
224 beamsplitter
226 movable polarization beamsplitter
227 movable mirror
228 target aperture
229 LED
230 light source
231 light source
232 aperture
233 aperture
234 lens
236 aperture
236a' image of aperture
236b' image of aperture
240 light source
242 light source
246 aperture
246a' image of aperture
246b' image of aperture
248 aperture
250 image
251 lens
252 image
254 image
260 display
261 cursor
262 thumbnail image
292 fiber optic ring
294 light source
300 automated imaging sequence
310 patient positioning step
320 alignment step
330 focus cornea step
336 adjust settings step
340 focus step
350 image capture step
400 operator
402 patient
406 motor
408 motor assembly
410 indicator element
412 aperture
414 aperture
416 switch
420 beamsplitter
422 sensor
430 folding element
432 sensor device
434 sensor device
435 spatial light modulator
436 polarizer
438 analyzer
440 sensor
442 beamsplitter
444 prism pair
446 sensor field
448 optical fiber
450 cornea focus detection section
452 retina focus detection section

The invention claimed is:

1. An apparatus for obtaining a retinal image from an eye, comprising:
   a) a control logic processor for executing a sequence of operations for obtaining the image;
   b) a visual target for orienting the eye of a patient when the target is viewed by the patient, the visual target comprising an aiming target aperture and a visible light source of an alignment assembly;
   c) a sensing device for providing a signal that indicates that the patient is in position for imaging;
   d) a cornea focus detection section for providing an indication of cornea focus, in cooperation with the control logic processor;
   e) an alignment actuator for aligning an optical path of the apparatus according to a signal obtained from the cornea focus detection section;
   f) a retina focus detection section for detecting retina focus in cooperation with the control logic processor;
   g) a focusing actuator controlled by instructions from the control logic processor according to a signal obtained from the retina focus detection section; and
   h) an image capture light source energized by the control logic processor for illuminating the retina for image capture.

2. An apparatus according to claim 1 wherein the signal is provided by the sensing device prior to activation of the cornea focus detection section.

3. An apparatus according to claim 1 wherein the control logic processor executes the sequence of operations in an automated manner, initiated upon receiving the signal from the indicator element.

4. An apparatus according to claim 1 wherein the cornea focus detection section comprises:
   a) an aperture element alternately illuminated from first and second light sources, wherein the first and second light sources are switched alternately on and off;
   b) a lens assembly for imaging the aperture element onto the cornea;

c) a cornea sensor for sensing the aperture element image on the cornea and providing sensed cornea image data to the control logic processor; and d) an actuator for adjusting the focus position of components in an imaging path, the actuator controlled according to instructions from the control logic processor, based on the sensed cornea image data.

5. An apparatus according to claim 4 wherein the first and second light sources are leds.

6. An apparatus according to claim 4 wherein the cornea sensor comprises a charge-coupled device sensor.

7. An apparatus according to claim 4 wherein the cornea sensor comprises a cmos sensor.

8. An apparatus according to claim 1 wherein the retina focus detection section comprises:
   a) an aperture alternately illuminated from first and second light sources;
   b) a lens assembly for imaging the aperture onto the retina;
   c) a retina sensor for sensing an image of the retina and providing sensed retina image data to the control logic processor; and
   d) a focus actuator for adjusting the focus position of components in an imaging path, the focus actuator controlled according to instructions from the control logic processor, based on the sensed retina image data.

9. An apparatus according to claim 8 wherein the first and second light sources are leds.

10. The retina focusing section of claim 8 wherein the first and second light sources are formed by a prism pair.

11. The retina focusing section of claim 8 wherein at least one of the first and second light sources is directed through an optical fiber.

12. An apparatus according to claim 1 wherein the cornea focus detection section comprises:
   a) at least one focus detection light source;
   b) a spatial light modulator for sequentially transmitting light from the focus detection light source through each of a plurality of openings in an aperture element to provide alternating illumination beams;
   c) a lens assembly for imaging the aperture element onto the cornea;
   d) a cornea sensor for sensing the aperture element image on the cornea and providing sensed cornea image data to the control logic processor; and
   e) an actuator for adjusting the focus position of components in an imaging path, the actuator controlled according to instructions from the control logic processor, based on the sensed cornea image data.

13. An apparatus according to claim 12 wherein the spatial light modulator is a liquid crystal device.

14. An apparatus according to claim 1 wherein the retina focus detection section comprises:
   a) at least one focus detection light source;
   b) a spatial light modulator for sequentially transmitting light from the focus detection light source through each of a plurality of openings in an aperture element to provide alternating illumination beams;
   c) a lens assembly for imaging the aperture element onto the retina;
   d) a retina sensor for sensing an image of the retina and providing sensed retina image data to the control logic processor; and
   e) a focus actuator for adjusting the focus position of components in an imaging path, the focus actuator controlled according to instructions from the control logic processor, based on the sensed retina image data.

15. The apparatus of claim 1, wherein the signal initiates an automated eye alignment process.

16. The apparatus of claim 1, wherein the sensing device comprises a sensor configured to automatically detect the proximity of the patient relative to a component of the apparatus.

17. The apparatus of claim 1, wherein the aiming target aperture is disposed between the visible light source and a first beamsplitter of the alignment assembly.

18. The apparatus of claim 17, wherein the alignment assembly further comprises a first lens assembly disposed between the aiming target aperture and the first beamsplitter.

19. The apparatus of claim 17, wherein the alignment assembly further comprises a second beamsplitter moveable relative to the first beamsplitter.

20. The apparatus of claim 19, wherein the second beamsplitter is a polarization beamsplitter.

21. The apparatus of claim 1, wherein the alignment assembly is configured to deliver a beam of collimated light to the eye of the patient to assist in orienting the eye to a position providing visual accommodation.

22. The apparatus of claim 1, wherein the visible light source of the alignment assembly is disposed along the optical path of the apparatus.

23. The apparatus of claim 1, wherein the alignment assembly is configured to assist in setting a position of the eye of the patient along the optical path of the apparatus.

* * * * *